United States Patent
Niedzwiecki et al.

(10) Patent No.: US 11,304,922 B1
(45) Date of Patent: Apr. 19, 2022

(54) PHARMACEUTICAL MICRONUTRIENT COMPOSITION FOR SIMULTANEOUSLY TREATING NERVOUS SYSTEM FUNCTION, COGNITIVE ABILITY AND RESPONSE TO STRESSORS

(71) Applicant: Matthias W Rath, Henderson, NV (US)

(72) Inventors: Aleksandra Niedzwiecki, Henderson, NV (US); Matthias W Rath, Henderson, NV (US); Parthena Boulikas, Sanjose, CA (US); Anna Goc, Sanjose, CA (US)

(73) Assignee: Matthias W. Rath, Henderson, NV (US)

( * ) Notice: Subject to any disclaimer, the term of this patent is extended or adjusted under 35 U.S.C. 154(b) by 0 days.

(21) Appl. No.: 17/552,189

(22) Filed: Dec. 15, 2021

Related U.S. Application Data

(63) Continuation of application No. 17/373,335, filed on Jul. 12, 2021, now Pat. No. 11,234,952.

(51) Int. Cl.
| | |
|---|---|
| A61K 31/198 | (2006.01) |
| A61K 36/899 | (2006.01) |
| A61K 36/23 | (2006.01) |
| A61K 36/41 | (2006.01) |
| A61K 31/122 | (2006.01) |
| A61K 36/738 | (2006.01) |
| A61K 36/258 | (2006.01) |
| A61K 31/4745 | (2006.01) |
| A61K 36/48 | (2006.01) |
| A61K 31/205 | (2006.01) |
| A61K 36/68 | (2006.01) |

(52) U.S. Cl.
CPC .......... *A61K 31/198* (2013.01); *A61K 31/122* (2013.01); *A61K 31/205* (2013.01); *A61K 31/4745* (2013.01); *A61K 36/23* (2013.01); *A61K 36/258* (2013.01); *A61K 36/41* (2013.01); *A61K 36/48* (2013.01); *A61K 36/68* (2013.01); *A61K 36/738* (2013.01); *A61K 36/899* (2013.01)

(58) Field of Classification Search
None
See application file for complete search history.

(56) References Cited

U.S. PATENT DOCUMENTS

| | | | |
|---|---|---|---|
| 7,670,612 B2 * | 3/2010 | Miller | A61K 9/4833 424/400 |
| 2021/0220422 A1 * | 7/2021 | Parker | A23L 33/15 |

* cited by examiner

*Primary Examiner* — Susan Hoffman
(74) *Attorney, Agent, or Firm* — Geeta Kadambi; Riddhi IP LLC

(57) ABSTRACT

A pharmaceutical composition of micronutrients were tried to improve cognitive brain function, brain health and nervous system functions. Combination consisting of *Avena sativa* (green oat straw extract), Coenzyme Q10, NAD+, American Ginseng, and Pyrroloquinoline quinone in physiological dose range shows multiple simultaneous positive effects in supporting key functions in cells building our nervous system essential for optimum mental and/or cognitive health including protecting nervous system cells against various damaging factors, increasing ATP production, stimulating mitochondria biogenesis, increasing mitochondrial membrane potential, increasing mitochondrial functions (Complex I activity), exhibiting anti-inflammatory capacity and increased BDNF secretion.

9 Claims, 24 Drawing Sheets

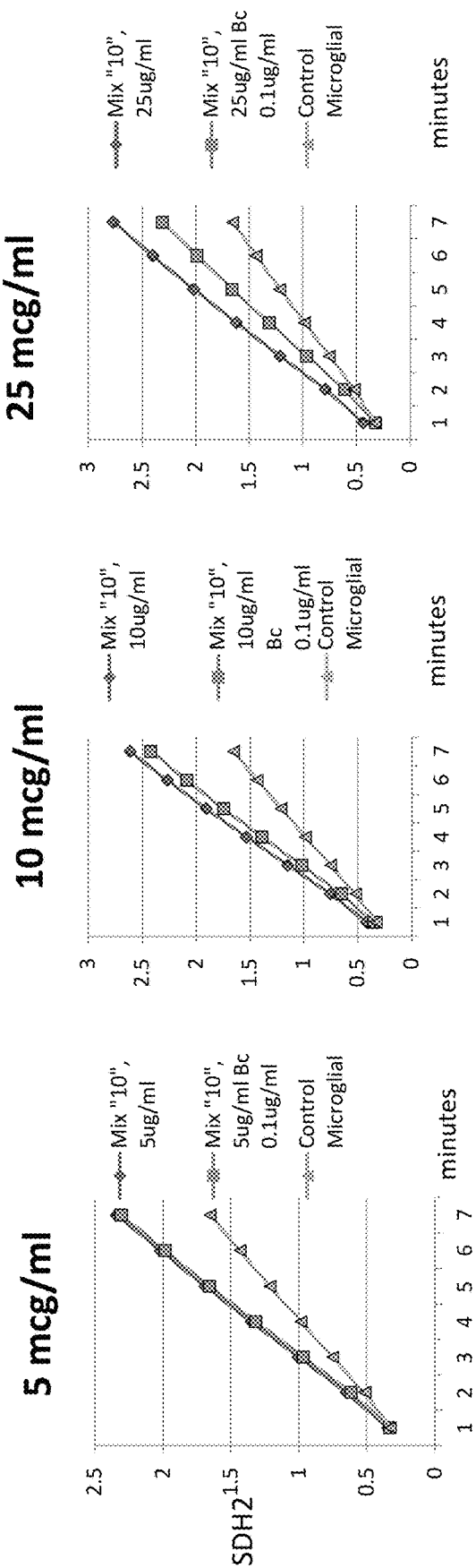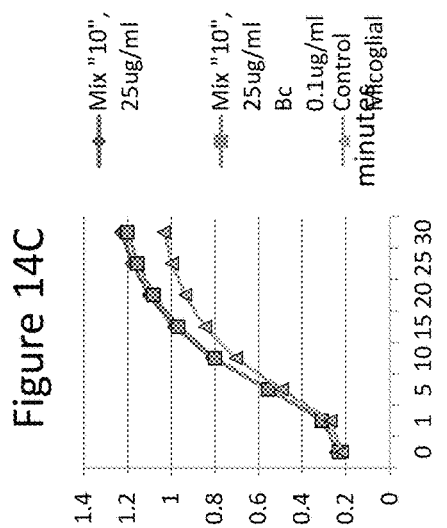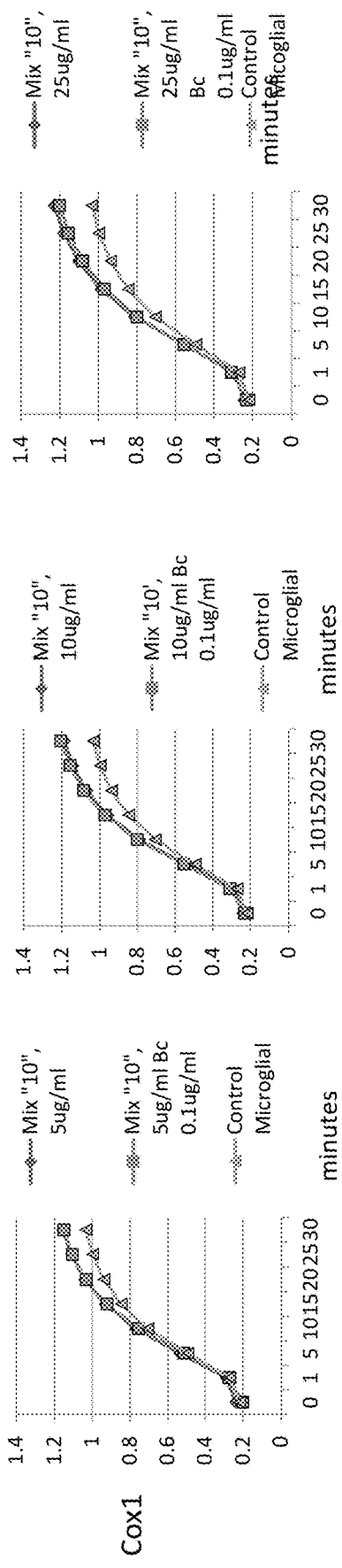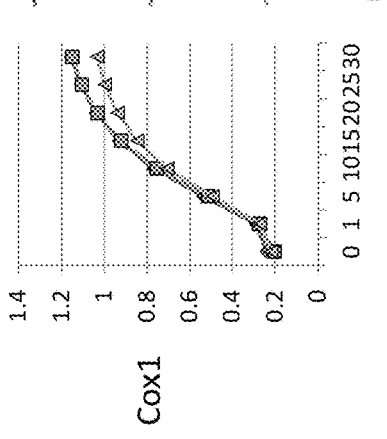

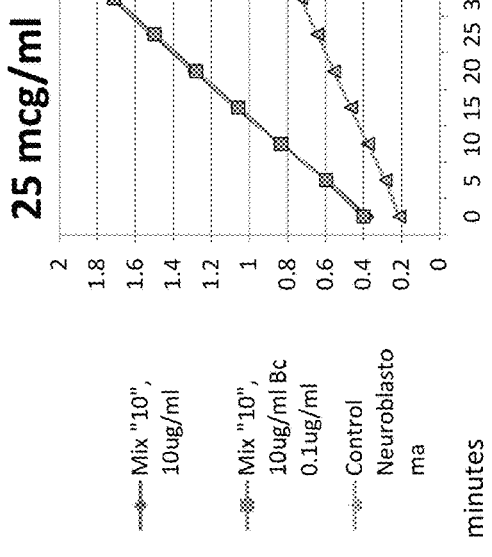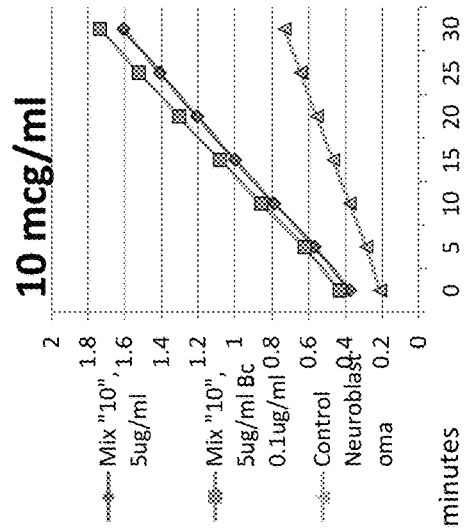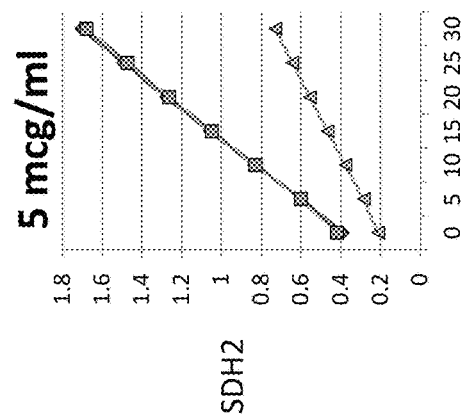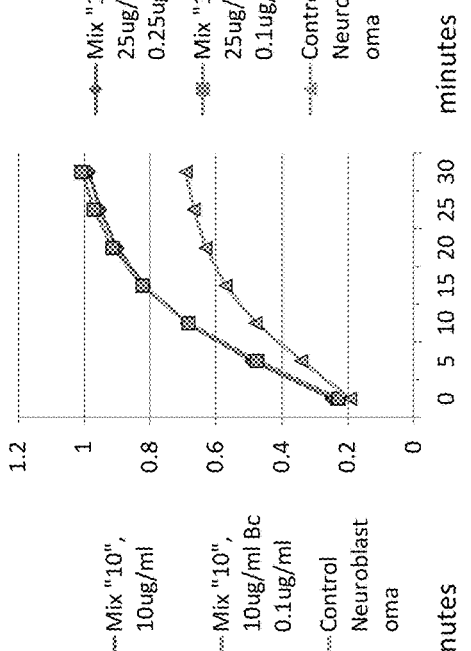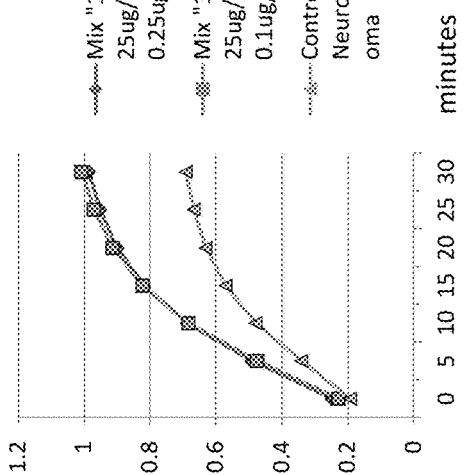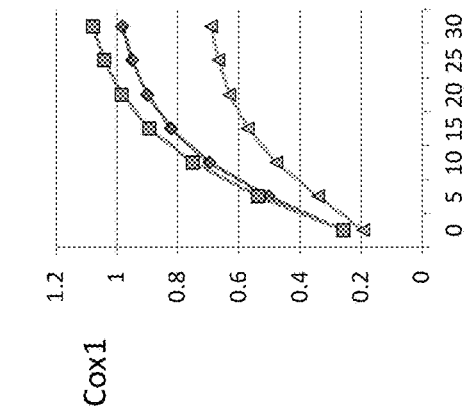
Figure 16A   Figure 16B   Figure 16C
Figure 17A   Figure 17B   Figure 17C

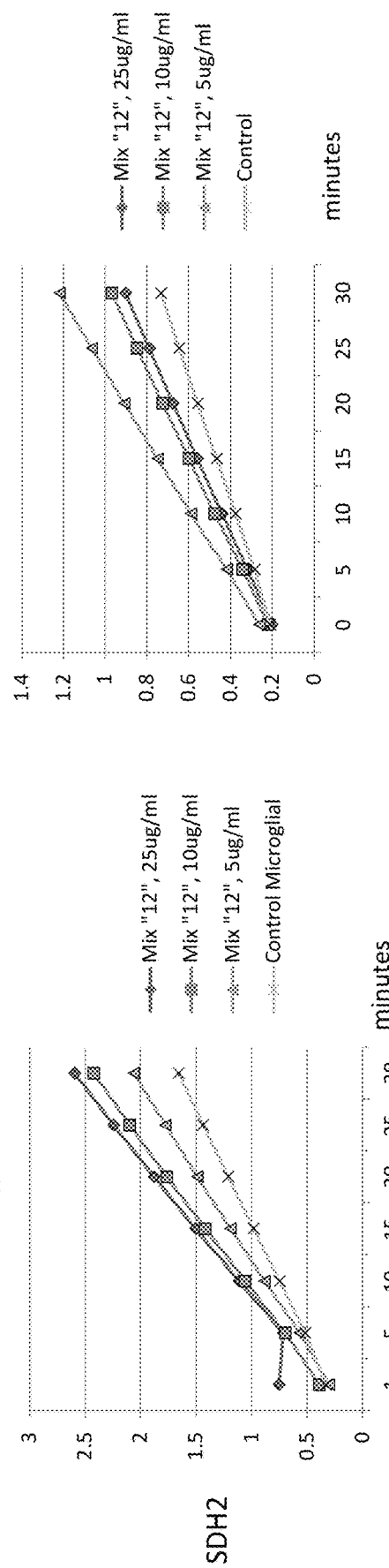
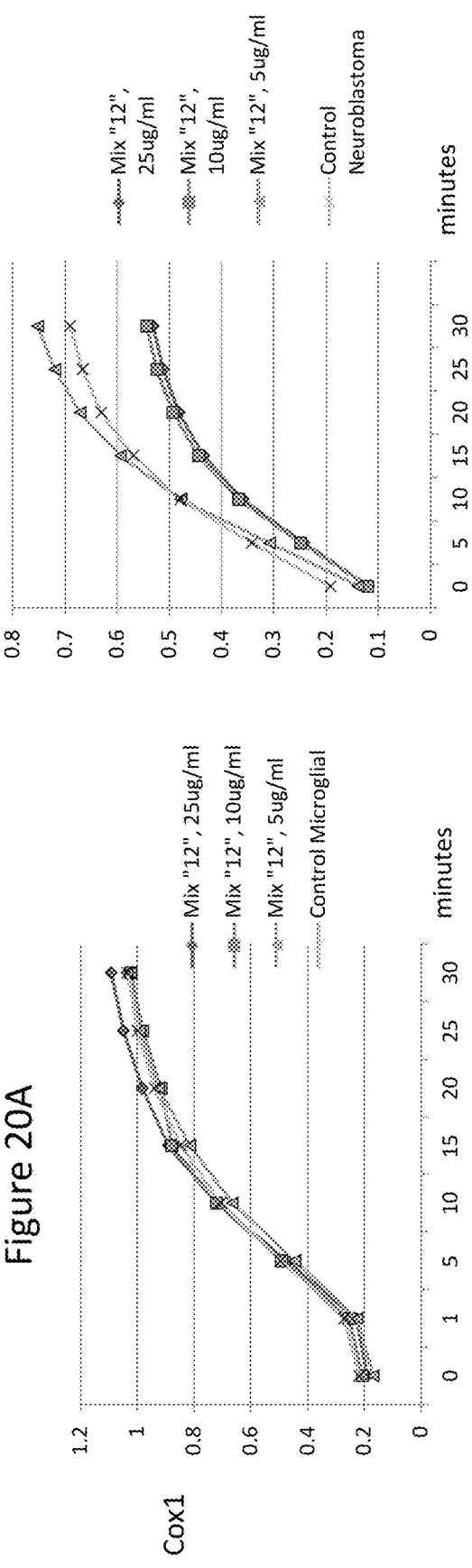
Figure 20A
Figure 20B
Figure 21A
Figure 21B

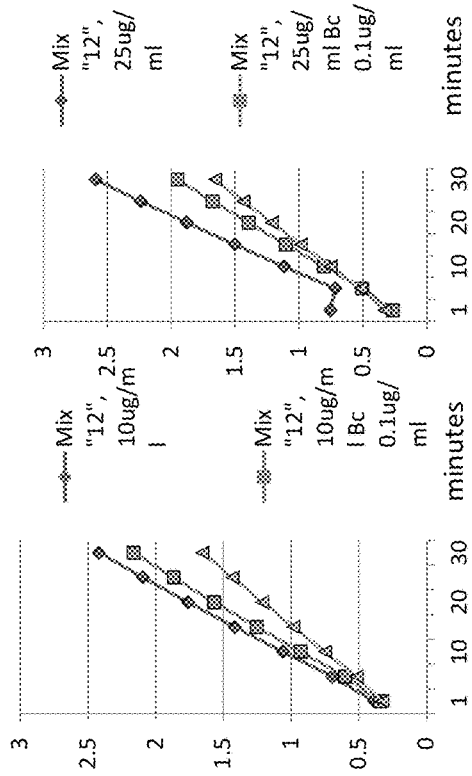
Figure 24A
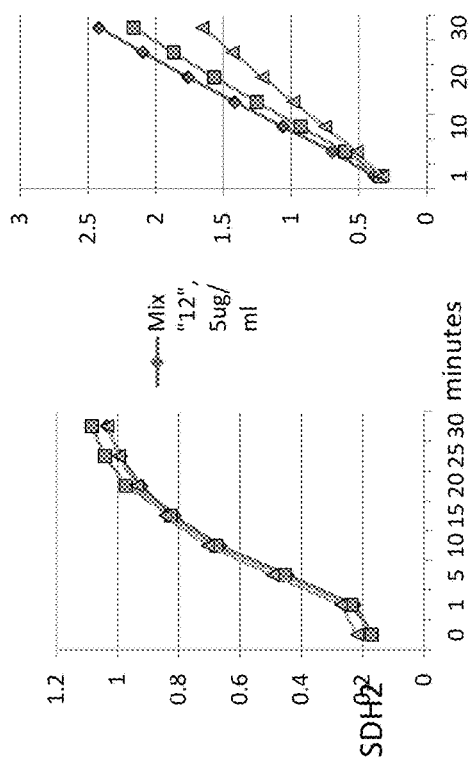
Figure 25A
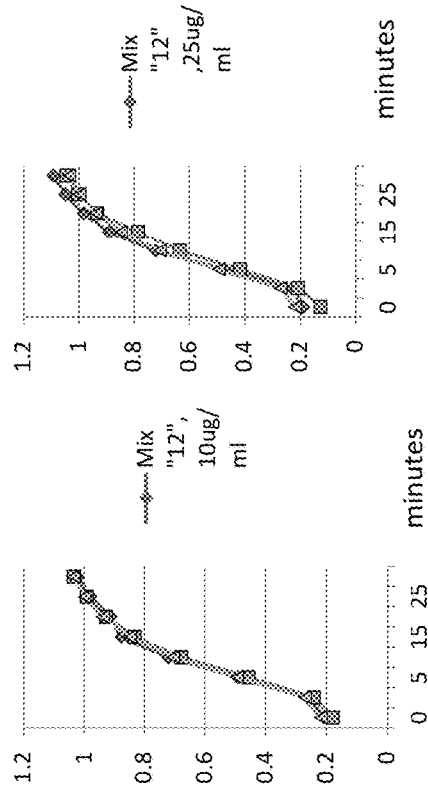
Figure 24B
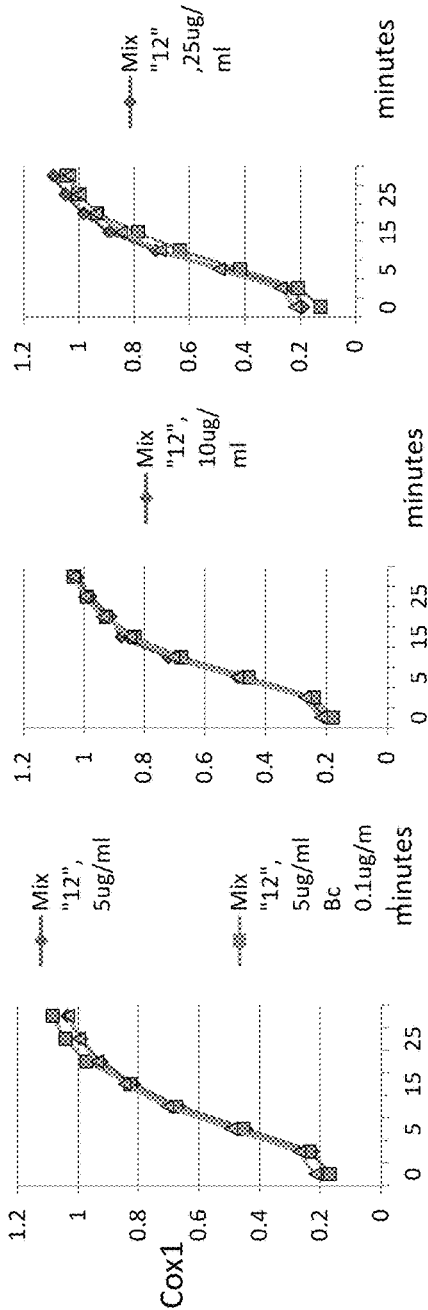
Figure 25B
Figure 24C
Figure 25C

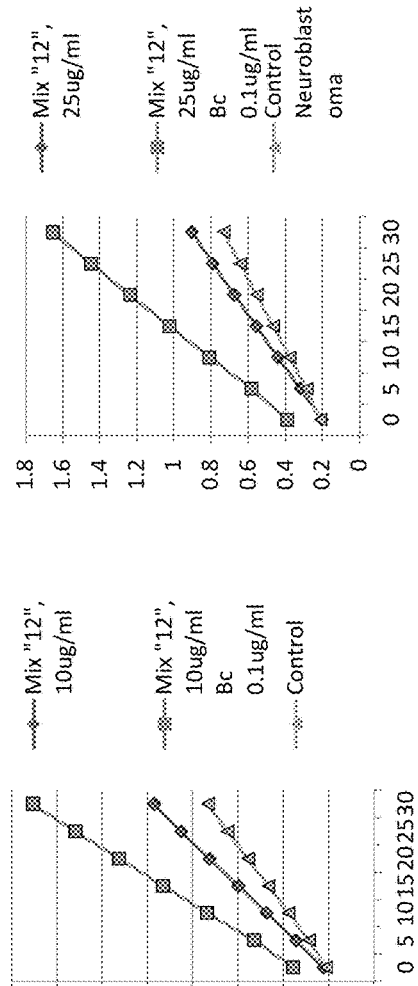
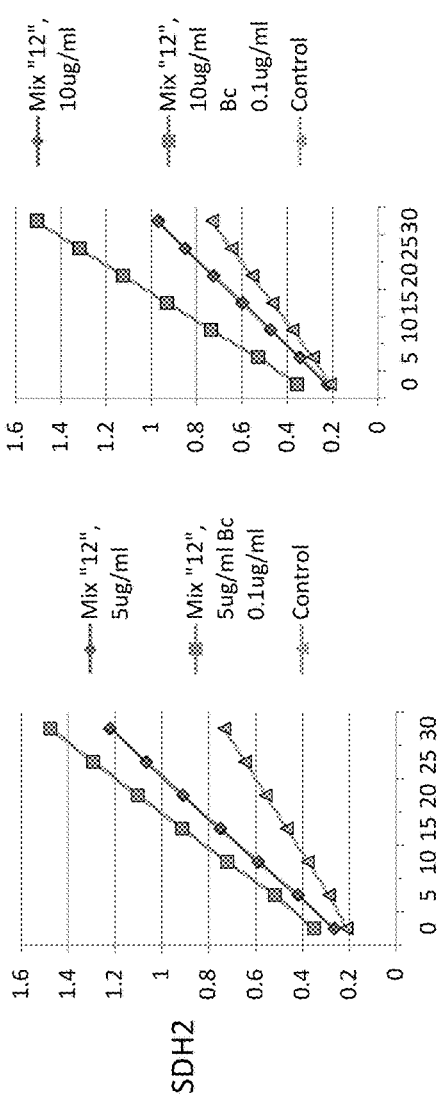
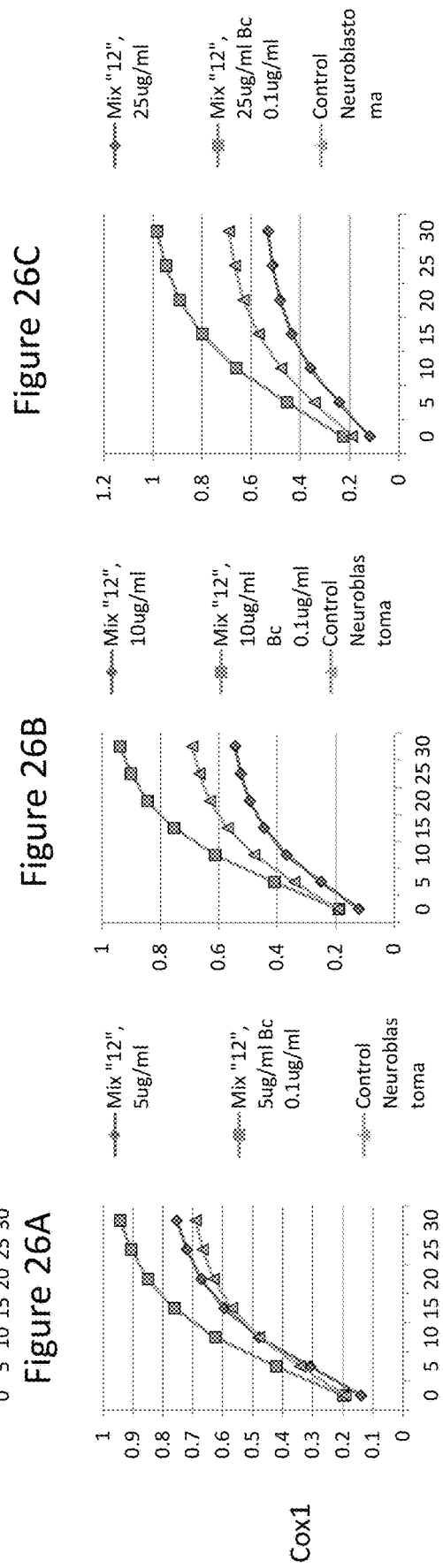
Figure 26A  Figure 26B  Figure 26C
Figure 27A  Figure 27B  Figure 27C

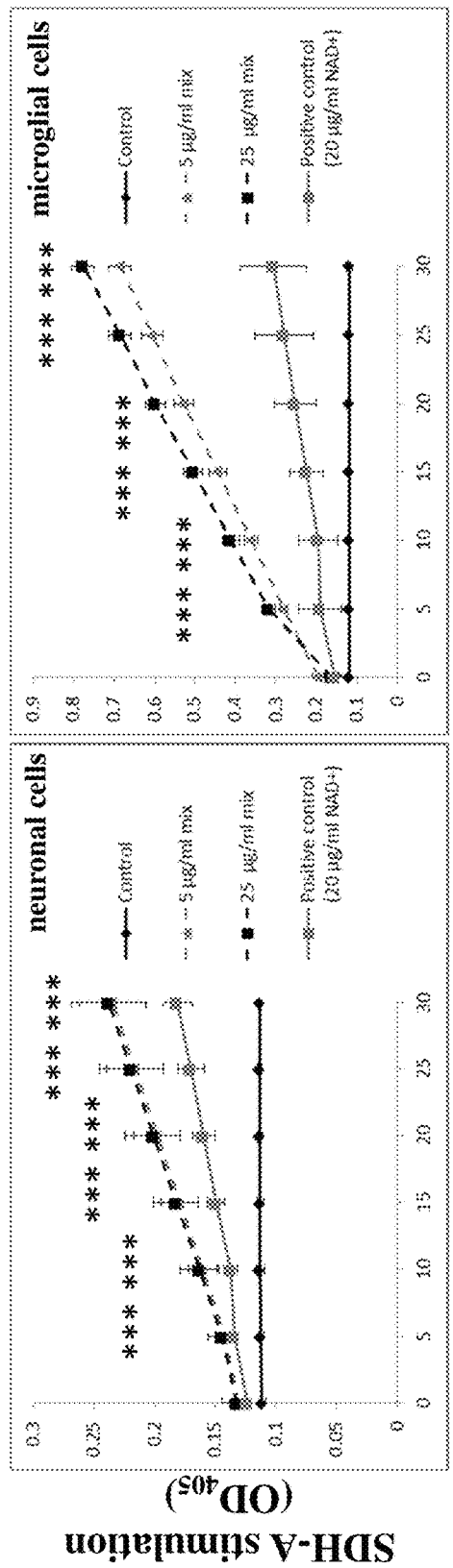
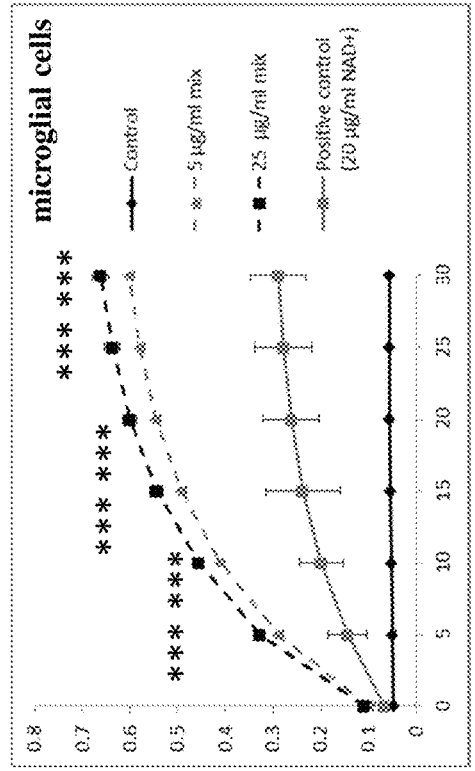
Figure 29A
Figure 29B
Figure 29C
Figure 29D

US 11,304,922 B1

PHARMACEUTICAL MICRONUTRIENT COMPOSITION FOR SIMULTANEOUSLY TREATING NERVOUS SYSTEM FUNCTION, COGNITIVE ABILITY AND RESPONSE TO STRESSORS

CROSS REFERENCE TO RELATED APPLICATIONS

This application is a continuation of U.S. application Ser. No. 17/373,335 filed on Jul. 12, 2021 which is now U.S. Pat. No. 11,234,952. The disclosure of U.S. application Ser. No. 17/373,335 is hereby incorporated by this reference in their entirety for all of their teachings.

FIELD OF STUDY

This application discloses new micronutrient composition for cognitive health, brain health and improvement of nervous system function.

BACKGROUND

Inflammation affects brain/body functioning and has been associated with a wide range of mental problems, poor memory, depression, and exaggerated responses to pain. Inflammation is accompanied by increased cytokine production which mediates the communication process to the central nervous system. Cytokines in the bloodstream cross the brain-blood barrier by active transport in regions where the barrier is weak. Among various cytokines and inflammatory mediators IL-6 induces synthesis of acute phase proteins such as CRP, serum amyloid A, fibrinogen, and inhibits production of albumin. Blockade of interleukin-6 by the specific anti-IL-6 receptor monoclonal antibody has been approved for the treatment of inflammatory diseases. We tested the efficacy of Formula 2 on inhibition of IL-6 secretion in neuronal and microglial cells exposed to a common inflammatory stimulant LPS and to a food additive MSG (monosodium glutamate), which has pro-inflammatory properties.

SUMMARY

In the instant disclosure various combination of micronutrients as pharmaceutical composition were used to treat, prevent, support and enhance brain health and nervous system function. In one embodiment a physiological dose for a mammal was calculated based on daily consumption. The formula was packaged in drug formulation for easy consumption.

In one embodiment, the pharmaceutical micronutrient composition consists of the an *Avena sativa* (green oat straw extract) in the range of 1 mg to 50,000 mg, CoQ10 in the range of 10 mcg to 20,000 mg, NAD+ in the range of 0.1 mg to 20,000 mg, American Ginseng in the range of 1 mg to 50,000 mg, and Pyrroloquinoline quinone in the range of 0.1 mg to 50,000 mg.

In one embodiment, American Ginseng is from natural source as a whole plant and/or synthetic source and/or standardized extract/extract/or combination thereof.

In one embodiment, NAD is from a natural source and/or synthetic source or combination thereof, Pyrroloquinoline quinone is from a natural source and/or synthetic source or combination thereof. In one embodiment, the pharmaceutical micronutrient composition is used for a treatment of cognitive impairments, depression and other nervous system problems in the human and other species.

In one embodiment, the mental and/or cognitive impairment is linked to mitochondrial dysfunction. In one embodiment, the mental impairment is linked to dysfunction in BDNF secretion. In another embodiment, the mental and/or cognitive impairment is linked to exposure to excessive stress (mental and chemical).

In one embodiment, the pharmaceutical micronutrient composition is used for maintaining healthy function of the nervous system in the human and other species. In one embodiment, the pharmaceutical micronutrient composition is used for preventing and mitigating the decline in cognitive and behavioral abilities due to age and other external and internal factors.

BRIEF DESCRIPTION OF DRAWINGS

Example embodiments are illustrated by way of example and not limitation in the figures of the accompanying drawings, in which like references indicate similar elements and in which:

FIGS. 14A, 14B and 14C shows effects of combination of different concentrations of formula 10 with B complex on mitochondrial biogenesis in microglial cells.

FIGS. 15A, 15B and 15C shows effects of combination of different concentrations of formula 10 with B complex on COX-1 in microglial cells.

FIGS. 16A, 16B and 16C shows effects of combining different concentrations of Formula 10 with B complex on mitochondrial biogenesis in neuronal cells.

FIGS. 17A, 17B and 17C shows Effects of combining different concentrations of Formula 10 with B complex on COX-1 in neuronal cells.

FIGS. 20A and 20B shows effects of Formula 12 on mitochondrial biogenesis in microglial cells and neuronal cells.

FIGS. 21A and 21B shows effects of Formula 12 on COX-1 mitochondrial biogenesis in microglial cells and neuronal cells.

FIGS. 24A, 24B and 24C shows effect of adding B complex for improving the efficacy of Formula 12 on mitochondrial biogenesis in microglial cells.

FIGS. 25A, 25B and 25C shows effect of adding B complex for improving the efficacy of Formula 12 on COX-1 mitochondrial biogenesis in microglial cells.

FIGS. 26A, 26B and 26C shows effect of adding B complex for improving the efficacy of Formula 12 on mitochondrial biogenesis in neuronal cells.

FIGS. 27A, 27B and 27C shows effect of adding B complex for improving the efficacy of Formula 12 on COX-1 mitochondrial biogenesis in neuronal cells.

FIGS. 29A, 29B, 29C and 29D shows formula 5 significantly stimulates mitochondrial biogenesis in neuronal and microglial cells.

Figure 1:
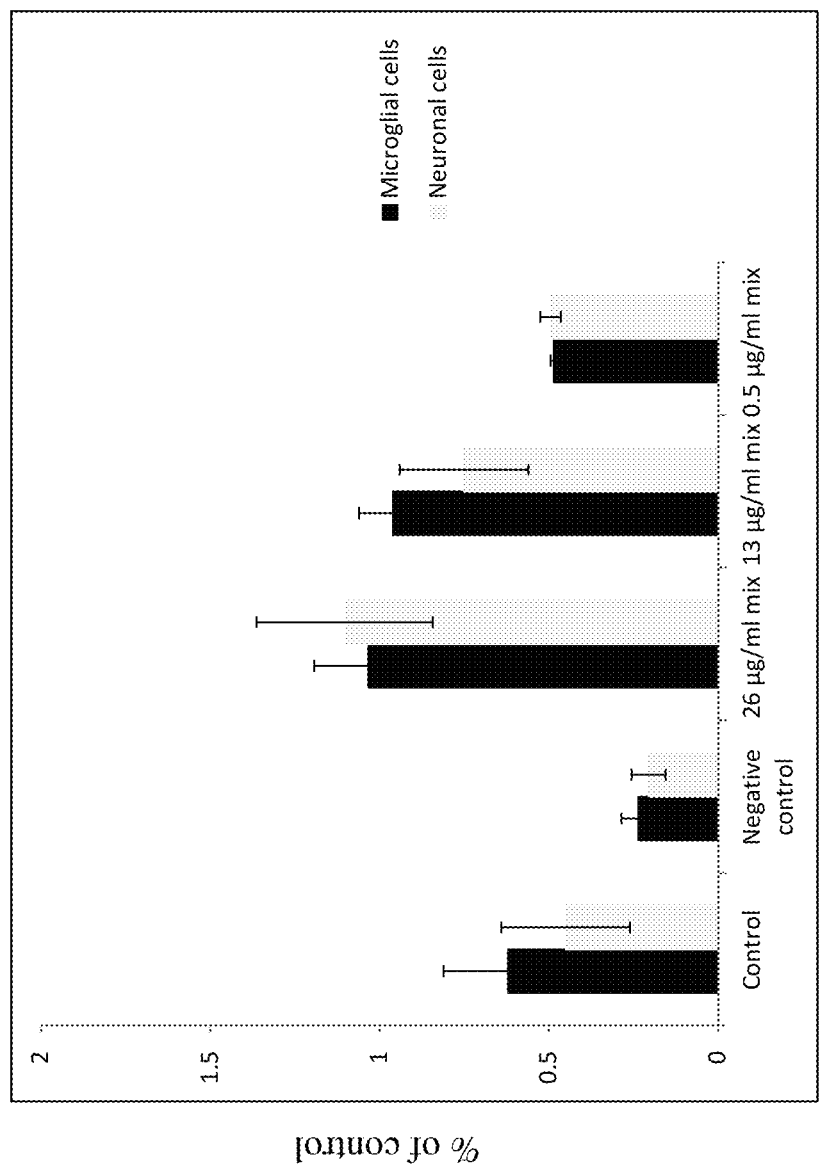
FIG. 1 shows cellular safety for formula 10 when viability test were performed.

Others features of the present embodiments will be apparent from the accompanying drawings and from the detailed description that follows.

DETAILED DESCRIPTION

The instant disclosure shows various combinations of pharmaceutical micronutrient composition and their effect on cellular and subcellular level effect on nervous system function, coping with stress, cognitive ability and general mental and/or cognitive health along with relevant cellular processes: bioenergy production, mitochondrial biogenesis, resistance to oxidative stressors, anti-inflammatory effects and increased neuroplasticity. The pharmaceutical micronutrient compositions are specifically mentioned as formula 12, formula 10 and formula 5 throughout the description. Various formulas such as formula 10, formula 12 and formula 5 were tested with various combinations of natural compounds as nutrients such as polyphenols, vitamins and minerals, plant extracts, amino acids and others. The concentration varied from 0.0005-1000 µg/ml. Formula 12 has 12 ingredients, formula 10 has 10 ingredients, and formula 5 has 5 ingredients common to formula 12 and formula 10.

TABLE 1 shows various combinations of pharmaceutical micronutrient composition:

| FORMULA 12 | FORMULA 10 | FORMULA 5 |
|---|---|---|
| L-Theanine | L-Theanine | |
| ALCAR (Acetyl L-Carnitine) | ALCAR (Acetyl L-Carnitine) | |
| Rhodiola rocea extract | Rhodiola rocea extract | |
| Bacoba monnieri | Bacoba monnieri | |
| Mucuna pruniens (seed extract) | Mucuna pruniens (seed extract) | |
| Gotu Kola | Gotu Kola | |
| NAD+ | NAD+ | NAD+ |
| Rose hip extract | Rose hip extract | |
| American Ginseng | American Ginseng | American Ginseng |
| Pyrroloquinoline quinone | Pyrroloquinoline quinone | Pyrroloquinoline quinone |
| Avena Sativa- oat | Avena Sativa oat | |

TABLE 1-continued shows various combinations of pharmaceutical micronutrient composition:

| FORMULA 12 | FORMULA 10 | FORMULA 5 |
|---|---|---|
| straw extract | | straw extract |
| Coenzyme Q10 | | Coenzyme Q10 |

Several experiments were done based on the following plans: The Formulas efficacy tests included processes important for nervous system function such as: bioenergy production, mitochondrial function, resistance to oxidative stressors, anti-inflammatory effects and neuroplasticity in neuronal and glial cell types: The tests showed:

Safety of micronutrients: no cell toxicity, no cell DNA damage (8-deoxyguanosine level)

Protection against oxidative/chemical stress: AGE-damage (diabetes), doxorubicin, Ara-C (cytosine arabinoside)

Positive effects on mitochondrial function: mitochondrial biogenesis (COX1—mitochondrial complex V and Succinate Dehydrogenase activity (SDH) a part of mitochondrial complex II), mitochondrial membrane potential, Complex I activity.

Improved Bioenergy: ATP Synthesis.

Anti-inflammatory effects: secretion of IL-6 after exposure to monosodium glutamate (MSG), Improved in neuroplasticity: BDNF secretion.

In the instant disclosure some of the micronutrients for polyphenols that was used and tested were Astaxantin, Urolithin A, Curcumin, Resveratrol and Pterostilbene. Vitamins and minerals were Vitamin C (ascorbyl palmitate), Sulbutiamine and Magnesium L-Threonate, plant extracts example are Tart cherry, Rosemary, *Rhodiola rosea* Hopes, Hawthorn, Astragalus, Gotu Kola, Celery, *Avena sativa*, Bacopa monnieri, Gingko biloba, Rose hips and *Mucuna pruriens*, amino acids such as NACA (N-acetylcysteine amid), NAC and L-theanine, others that were used were ALCAR, 7-keto-DHEA, Lipoic acid, L-sulforaphane, α-GPC, NAD+, NALT, Tauroursodeoxycholic acid, Cyanidin-3-glucoside Sapropterin, Tianeptine, Triacetyluridine, Uridine monophosphate, S-Adenosyl Methionine, Inositol, Huperzine A, CoQ10, Pyrroloquinoline quinone, CDP-choline, Centrophenoxin, D-ribose, DMAE Bitartrate, Gastrodin, and Glucuronolactone. From 48 natural compounds evaluated in the initial screening process, the most effective compounds were combined as more comprehensive formula 10, formula 12 and the formula 5 which contained key ingredients for the basic support for nervous system function.

Several tests were conducted on neuronal and glial cell types: Safety of nutrient combinations: maintained cell viability, no DNA damage (8-deoxyguanosine level), Protection against oxidative/chemical stress: AGE-damage (diabetes), doxorubicin, Ara-C (cytosine arabinoside).

Support of mitochondrial function by supporting:
  mitochondrial biogenesis evaluated by increase in COX1—(a part of mitochondrial complex V) and Succinate Dehydrogenase activity (SDH) (a part of mitochondrial complex II),
  mitochondrial membrane potential,
  Complex I activity
  Bioenergy: ATP synthesis Anti-inflammatory efficacy: secretion of IL-6 after exposure to proinflammatory factors: monosodium glutamate (MSG) and LPS BDNF secretion (neuroplasticity)

Formulas compounds were bought from:
L-theanine (Microingredients, Diamond Bar, Calif., USA)
*Rhodiola rosea* (extract standardized to 3% salidrosides) (Powder City, York, Pa., USA)
ALCAR (Acetyl L-Carnitine) (Bulk Supplements, Henderson, Nev., USA)
Bacopa monnieri plant (Banyan Botanicals, Albuquerque, N. Mex.)
*Mucuna pruriens* seed extract 20:1, (Microingredients, Diamond Bar, Calif., USA)
NAD+ (Cayman Chemicals, Ann Arbor, Mich., USA)
Rose hips extract (trans-tiliroside) (Bulk Supplements-.com, Henderson, Nev., USA)
American Gingseng (root) (Monterey Bay, Watsonville, Calif., USA)
Pyrroloquinoline quinone (Sigma-Aldrich, St. Louis, Mo., USA)
Gotu Kola *Centella asiatica* (fruit) (Bulk Supplements, Henderson, Nev., USA
*Avena sativa* (green oat straw extract) (Bulk Supplements, Henderson, Nev.)
Coenzyme Q10 (Sigma-Aldrich, St Louis, Mo.)
Pyrroloquinoline quinone (Sigma-Aldrich, St. Louis, Mo.)
Cell Cultures:
(IMG) Microglial Immortalized cells (mouse) from Kerafast (Boston Mass., USA)
(SH-SY5Y) Human neuronal cells (Neuroblastoma from human nerve) from ATCC (Manassas, Va., USA)
(RSC96) Schwann sciatic nerve cells (*Rattus norvegicus*) from ATCC, (Manassas, Va., USA).

Other reagents: Fetal Bovine Serum (FBS) from ATCC, Penicillin and Streptomycin (PS), and Trypsin-EDTA from Gibco. All other reagents were provided in respective test kits by the manufacturers or purchased from Sigma-Aldrich.

Cytotoxicity: Cells were grown in Dulbecco's modified Eagle's medium DMEM/10% FBS/1% PS. After 24 hrs the cells were trypsinized and plated into 96 well clear plates. Cells were allowed to attach for 24 hrs; then the seeding medium was removed and replaced by the same medium without FBS containing the test mixtures at concentrations 0.5, 13, and 26 µg/ml. Control contained cells with medium only and negative control contained cells exposed to $H_2O_2$ as a damaging agent. The viability of cells was evaluated by alamarBlue assay at 570 nm.

Cell protective capacity: Cells were grown in Dulbecco's modified Eagle's medium DMEM/10% FBS/1% PS. After 24 hrs the cells were trypsinized and plated into 96 well plates. Cells were allowed to attach for 24 hrs. Then the seeding medium was removed and replaced by the same medium without FBS containing the test mixtures at concentrations of 12.5 and 25 µg/ml. Control contained cells with medium only and cells exposed to $H_2O_2$ were used as negative control. The damaging agents tested were: AGE (Advanced Glycation End products) (875 µg/ml), Cytarabine (Ara-C) (25 µg/ml) and Doxorubicin (DOX) (25 µg/ml); all diluted in FBS free medium. After 48 hrs, the alamarBlue Viability Assay was performed by adding $1/10^{th}$ volume of alamarBlue reagent directly to cells in culture media. After incubation for 3 hrs at 37 degrees C., protected from light the absorbance was monitored at 570 nm.

ATP synthesis: The test cell lines were grown in Dulbecco's modified Eagle's medium DMEM/10% FBS/1% PS. After 24 hrs the cells were trypsinized and plated into 96 well clear or white plates. Cells were allowed to attach for 24 hrs; then the seeding medium was removed and replaced by the same medium without FBS containing the test mixtures at concentrations of 20, 10, 0.5 and 0.25 µg/ml. Control included cells with the medium only and negative control contained cells exposed to 1 mM $H_2O_2$. After 24 hrs the treated cells were subjected to Luminescent ATP detection Assay Kit (Luminescent ATP detection Assay kit, Ab113849) according to the manufacturer's protocol.

Mitochondrial Function: Complex I activity: The activity of Complex I in isolated mitochondria was evaluated using Cayman's MitoCheck® Complex I Activity Assay according to the manufacturer's protocol. Briefly, bovine brain mitochondria (provided in the kit) were suspended in Assay Buffer and exposed to the test mixtures at 10 and 25 µg/ml concentrations for 16 hrs at 25° C. Positive control contained CoQ10 (125 and 250 µg/ml). The rate of NADH oxidation was measured by a decrease in absorbance at 340 nm which is proportional to the activity of complex I.

Mitochondrial membrane potential: The effect of test formulas on mitochondrial membrane potential was evaluated by using Abcam 113852 TMRE Mitochondrial Membrane Potential Assay Kit which allows for quantifying changes in mitochondrial membrane potential in live cells by microplate spectrophotometry. The assay applies TMRE (tetramethylrhodamine, ethyl ester) which is a red-orange dye that readily accumulates in active mitochondria due to its relative negative charge. Depolarized or inactive mitochondria have decreased membrane potential and fail to sequester TMRE.

Briefly, the cells were grown in Dulbecco's modified Eagle's medium DMEM/10% FBS/1% PS for 24 hrs. After that they were trypsinized and plated into 96 well plates. Cells were attaching for 24 hrs. Subsequently, the seeding medium was removed and replaced by the same medium without FBS containing the test mixtures at 10 and 25 µg/ml for 16 hrs. Control contained cells without test compounds and negative control contained cells treated with 20 µg/ml FCCP ((carbonyl cyanide 4-(trifluoromethoxy) phenylhydrazone) as an uncoupler of oxidative phosphorylation). The plates were incubated for 10 min. and subsequently exposed to TMRE for 15-30 min. The media from adherent cells were removed and cells washed with PBS/0.2% BSA. The mitochondrial membrane potential was analyzed with microplate reader at Ex/Em=549/575 nm.

Mitochondrial Biogenesis: Mitochondrial biogenesis was evaluated using MitoBiogenesis In-Cell ELISA Assay (Abcam 110217) according to the manufacturer's protocol. This assay measures SDH-A protein which is a subunit of nDNA-encoded Complex II and COX-1 enzyme which is a mitochondria encoded part of subunit I in the Complex IV. All test cell lines were grown in in Dulbecco's modified Eagle's medium DMEM/10% FBS/1% PS. After 24 hrs the cells were trypsinized and plated into 96 well plates. Cells were attaching for 16 hrs at 37 degrees C. Then the seeding medium was removed and replaced by the same medium without FBS containing the test mixtures at the following concentrations: 5.0, 10 and 25 µg/ml. All plates were incubated for 16 hrs. Control cells contained 0.025% DMSO. Cells were exposed to anti-SDH-A and anti-COX-I monoclonal antibodies respectively for overnight at 4° C., washed and AP/HRP labelled secondary antibodies were added (100 µl per well). Subsequently, all plates were incubated for 1 hr at room temperature. The detection of SDH-A was based on kinetic mode of reading at 405 nm and for COX-1 at 650 nm for 30 minutes with 20 seconds intervals.

Anti-Inflammatory capacity: Effects of test mixtures on IL-6 secretion by microglial and neuronal cells were evaluated using Mouse Elisa from Abcam (ab 100712) kit. Test cells were grown in Dulbecco's modified Eagle's medium DMEM/10% FBS/1% PS. After 24 hrs they were trypsinized and plated into 96 well plates. Cells were allowed to attach for 24 hrs. As pro-inflammatory stimulants the cells were exposed to LPS and MSG.

LPS exposure: After cells attachment, the seeding medium was removed and replaced by the same medium without FBS containing the Formula 10 at concentrations of 10, 5, 1.5, 0.5 and 0.25 ug/ml for 24 hrs. Control contained cells with the medium and positive control contained 5 ng/ml LPS. After the incubation period the IL-6 level was evaluated according to the manufacturer's protocol.

MSG (monosodium glutamate) exposure: After cells attachment, the seeding medium was removed and replaced by the same medium without FBS containing the test mixtures at concentrations 1 and 0.5 µg/ml and MSG at concentrations 100, 50, 20 and 10 mM. After 24 hrs, the IL-6 level was evaluated according to the manufacturer's protocol.

BDNF-derived neurotrophic factor secretion: All three cell lines were grown in Dulbecco's modified Eagle's medium DMEM/10% FBS/1% PS. After 24 hrs the cells were trypsinized and plated into 96 well plates. Cells were left to attach for 16 hrs at 37 degrees C. Then the seeding medium was removed and replaced by the same medium and different concentrations of the test formulas. As such Formula 12 was applied at 10, 5, 1.5, 0.5 and 0.25 µg/ml, Formula 10 at 0.25 ug/ml and 0.5 ug/ml and formula 5 at 2.5 ug/ml and 7.5 µg/ml; all without FBS and in triplicates. Controls contained cells without test compounds and positive control contained curcumin at 25 µg/ml. The plates were incubated with the mixtures for 16 hrs at 37° C. after which the supernatants were collected from each sample in Eppendorf tubes and centrifuged for 10 minutes at 12,650 rpm.

The presence of BDNF in the cell culture supernatants was evaluated using RayBio® Rat BDNF ELISA kit for rat Schwann cells, Abnova Mouse BDNF ELISA KA0331 for mouse microglial cells and RayBio Human BDNF ELISA (ELH-BDNF) was used to evaluate BDNF in human neuronal cell line. All these assays employ an antibody specific for BDNF coated on a 96-well plate according to the manufacturer's protocols and the BDNF levels were evaluated by colorimetric detection at 450 nm.

FIG. 1 shows Microglial cell line (IMG) and neuronal cell line (SH-SY5Y) were treated with the Formula 10 for 24 hrs, and subjected to alamarBlue assay; As negative control: indicating dead cells were exposed to $H_2O_2$ (1 mM). No cytotoxic effects, just in contrary, the microglial and neuronal cells exposed to Formula 10 showed improved viability/growth.

Figure 2:
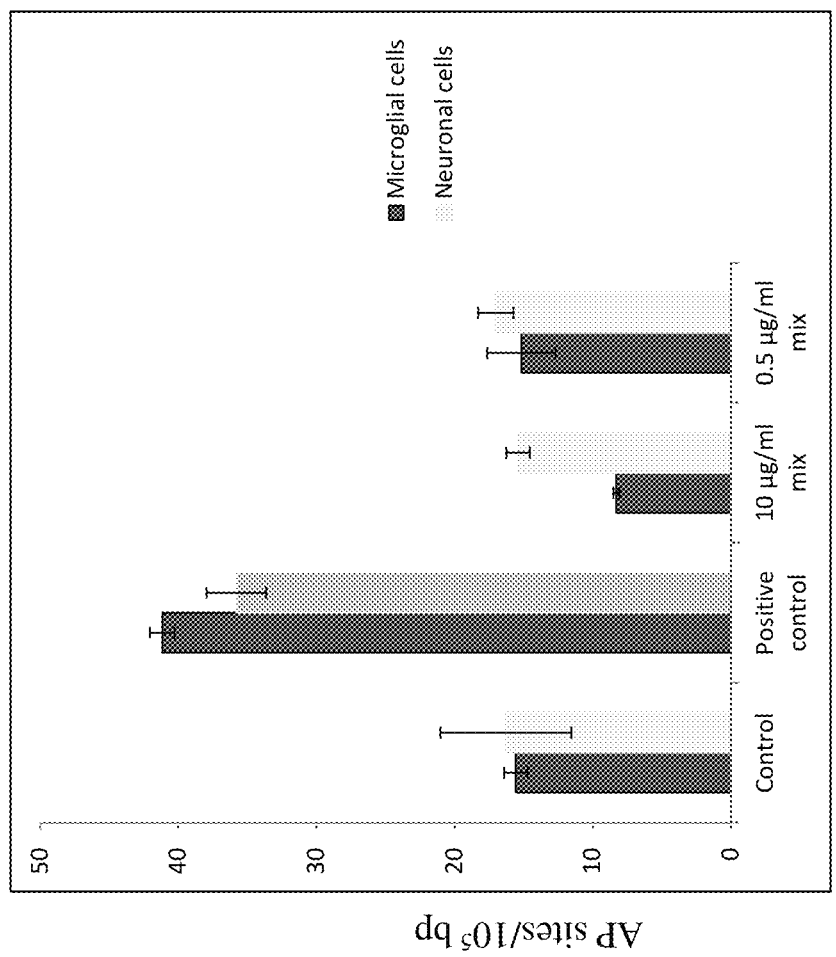
FIG. 2 shows resistance to oxidative damage by testing DNA damage using formula 10.

FIG. 2 shows DNA damage in microglial and neuronal cells was assessed by measuring 8-oxoguanidine. Microglial cell line (IMG) and neuronal cell line (SH-SY5Y) were treated with the Formula 10 for 24 hrs, followed by DNA isolation and measurement of DNA damage by number of apurinic/apyramidinic sites; positive control: DNA damage induced by 1 mM $H_2O_2$. Microglial and neuronal cells exposed to Formula 10 did not show any DNA damage compared to control.

Figure 3:
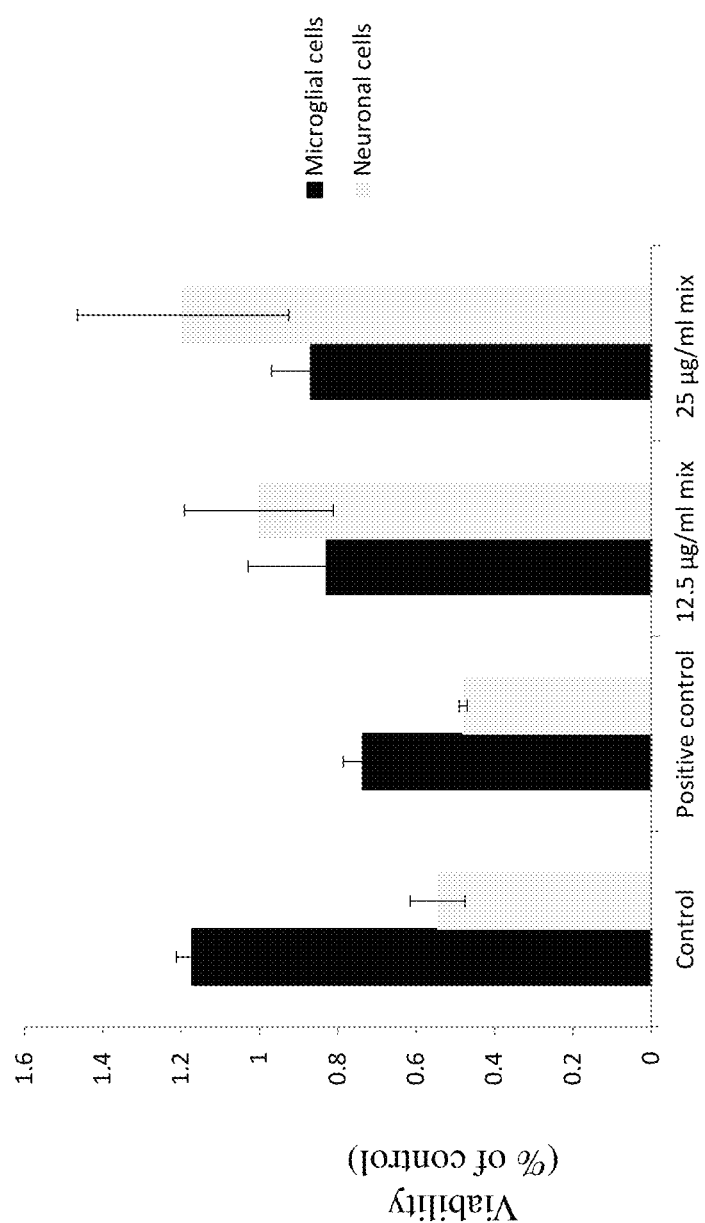
FIG. 3 shows protection against cell damage factors such as AGE proteins using formula 10.

FIG. 3 shows Microglial cell line (IMG) and neuronal cell line (SH-SY5Y) were pre-treated with Formula 10 for 24 hrs followed by adding 875 µg/ml AGE (positive control) and subjected to alamarBlue assay. Microglial and neuronal cells exposed to Formula 10 show high level of protection from damage induced by AGE proteins. Highest protection efficacy was observed in neuronal cells.

Figure 4:
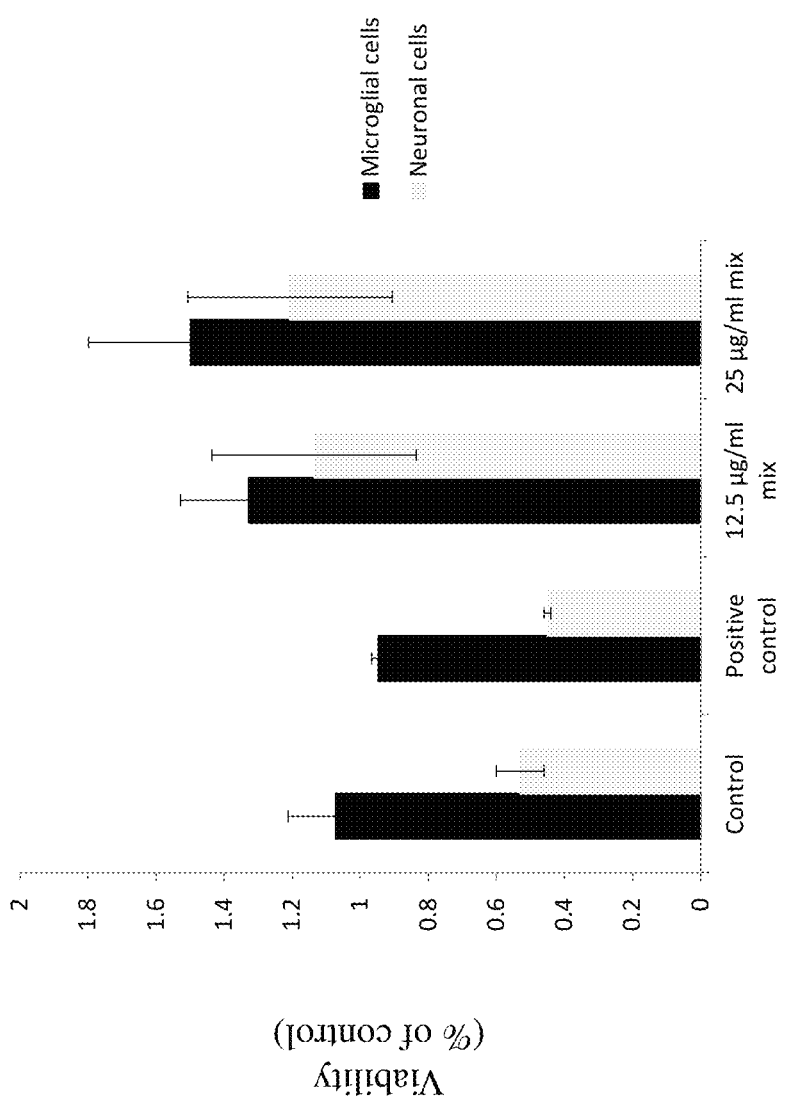
FIG. 4 shows cell protection against chemical toxins using formula 10.

FIG. 4 shows results of effects of Formula 10 on cell protection against Doxorubicin. Microglial cell line (IMG) and neuroblastoma cell line (SH-SY5Y) were pre-treated with the mix for 24 hours followed by adding 25 µg/ml DOX (positive control) and subjected to alamarBlue assay. Chemotherapy has negative impact on mental and/or cognitive health. Formula 10 shows protective effect in microglial and neuronal cells against damage caused by Doxorubicin (chemotherapy agent).

Figure 5:
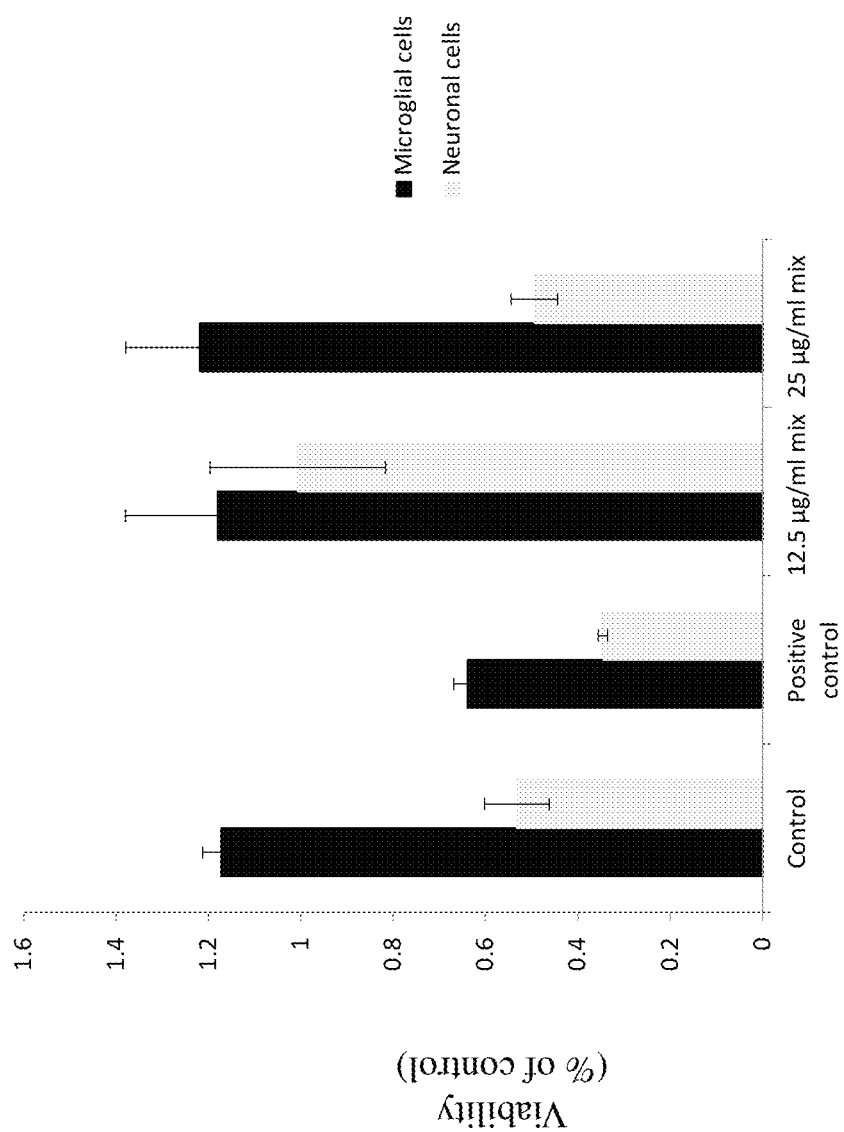
FIG. 5 shows cell protection against chemotherapy agents using formula 10.

FIG. 5 shows Microglial cell line (IMG) and neuronal cell line (SH-SY5Y) were pre-treated with the mix for 24 hrs followed by adding 25 µg/ml Ara-C. Positive control: cells with Ara-C only. Viability assessed by alamarBlue assay. Formula 10 shows protective effect in microglial and neuronal cells against damage caused by ARA-C (chemotherapy agent).

Figure 6A:
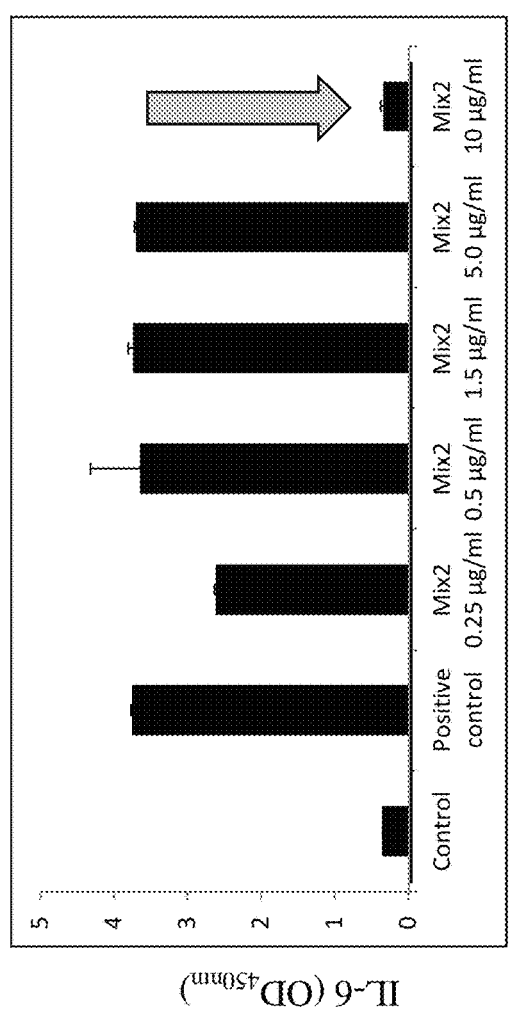
FIGS. 6A and 6B shows anti-inflammatory potential of formula 10. On the figure it is labelled as Mix 2.
Figure 6B:
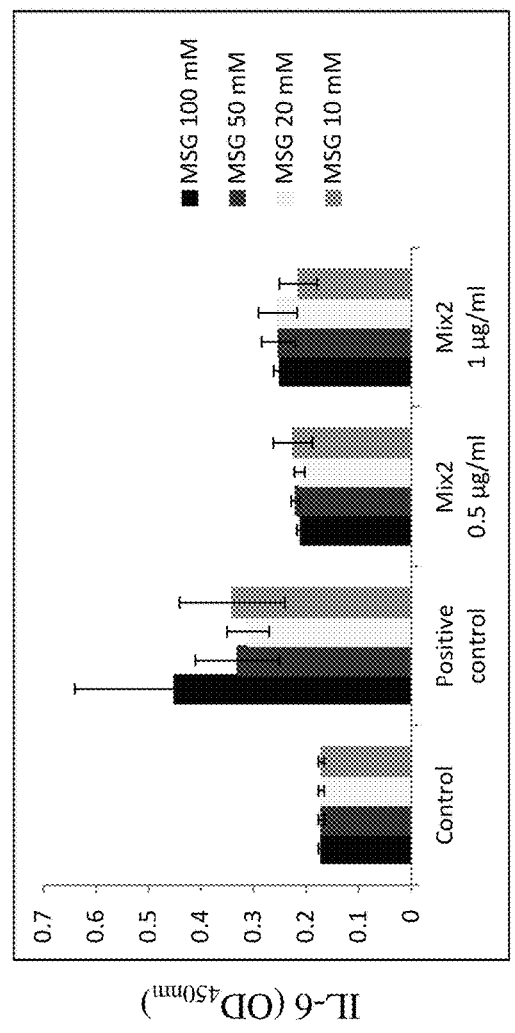
Figure 7B:
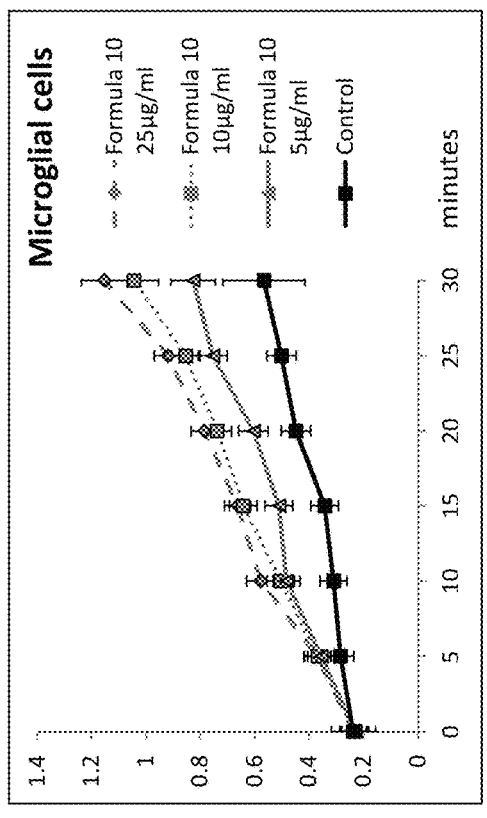
FIGS. 7A and 7B shows beneficial effect of formula 10 during mitochondrial biogenesis.
Figure 8B:
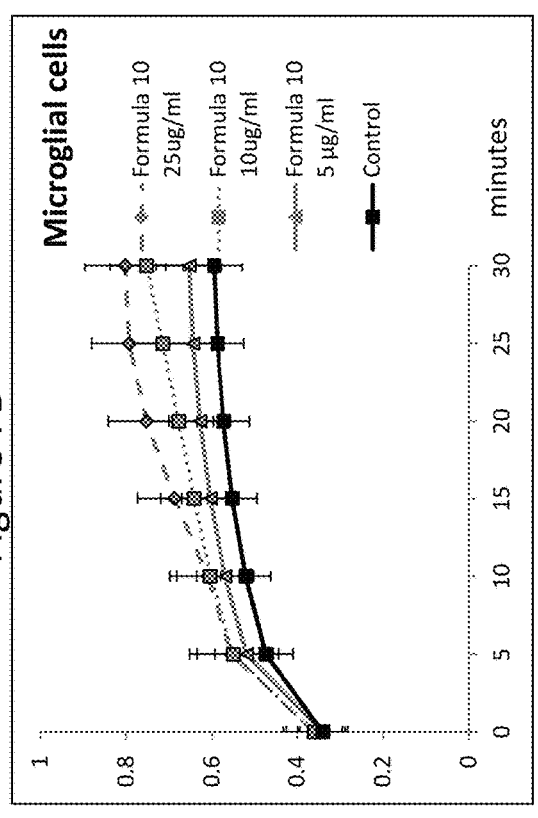
FIGS. 8A and 8B shows effect of formula 10 on COX-1 during mitochondrial biogenesis.
Figure 7A:
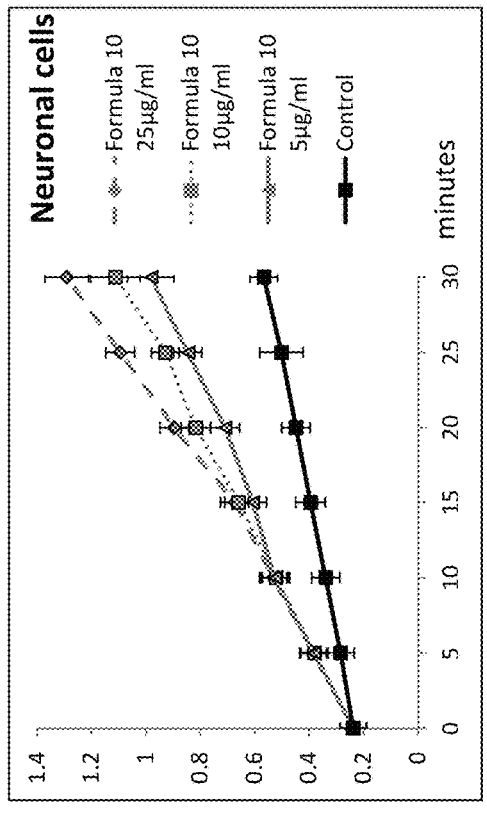
Figure 8A:
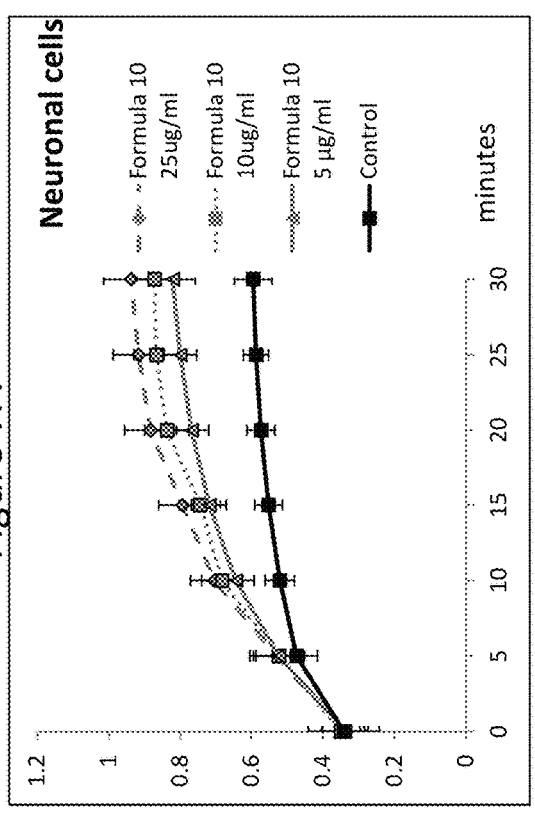

FIG. 6A shows Mouse microglial cells co-treated with the Mix 10 and LPS at 5 ng/ml for 24 hours, followed by measurement of IL-6 level; positive control: LPS at 5 ng/ml concentration and FIG. 6B shows mouse microglial cells co-treated with the Formula 10 and MSG for 24 hrs, followed by measurement of IL-6 level; positive control: MSG at 10, 20, 50, and 100 mM concentrations. Formula 10 decreased IL-6 secretion in microglial cells under pro-inflammatory stimulation with LPS and a food additive MSG. In this figure formula 10 has been labelled as Mix 2. Mix 2 represents formula 10 in the instant specification.

FIGS. 7A and 7B, and FIGS. 8A and 8B shows the effects of Formula 10 on mitochondrial biogenesis in neuronal and microglial cells. The respective cells were treated with the Mix 10 for 16 hrs, followed by measurement of their mtDNA-encoded COX-I protein and nDNA encoded SDH-A using MitoBiogenesis In-Cell ELISA kit; control—0.025% DMSO.

Mitochondrial efficacy and Complex I activity: Complex I is a large enzyme catalyzing the first step in electron transfer chain by transferring electrons from NADH to Coenzyme Q10. It establishes the hydrogen ion gradient by pumping four hydrogen ions across the membrane from the matrix into the intermembrane space. Its dysfunction is regarded as underlying dopamine neuron death in Parkinson's disease models, its activity decreases with aging.

Mitochondrial membrane potential: Mitochondrial membrane potential is a key indicator of mitochondrial activity because it reflects the process of electron transport and oxidative phosphorylation, the driving force behind ATP production.

Figure 9:
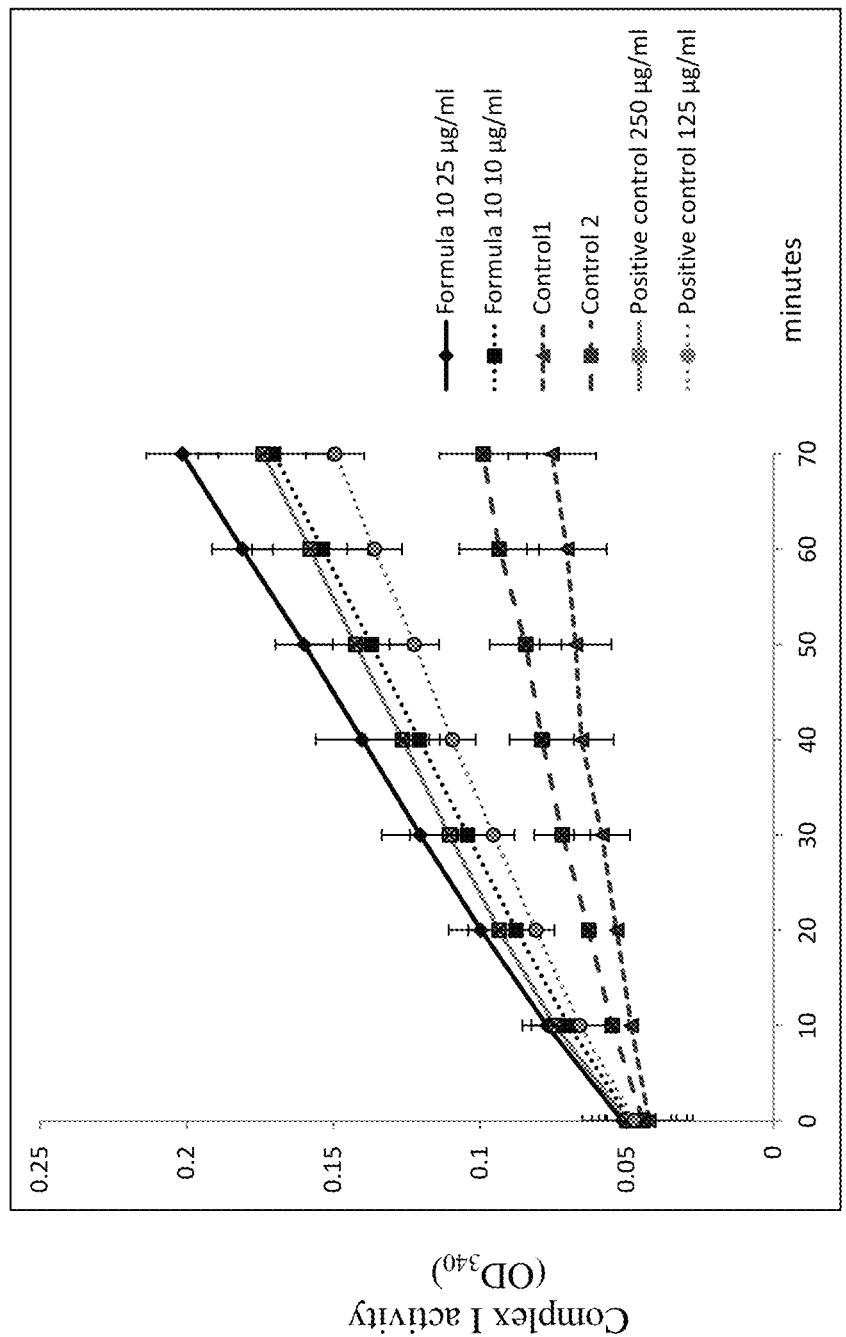
FIG. 9 shows formula 10 improving mitochondrial complex 1 activity.

FIG. 9 shows the effects of Formula 10 on Complex I activity. Brain mitochondria were treated with the Formula 10 for 16 hours, followed by measurement of Complex I activity using MitoCheck Complex I activity assay kit; positive control: $CoQ_{10}$, Control 1—0.01% DMSO, Control 2—0.025% DMSO. Formula 10 improves mitochondrial Complex I activity.

Figure 10:
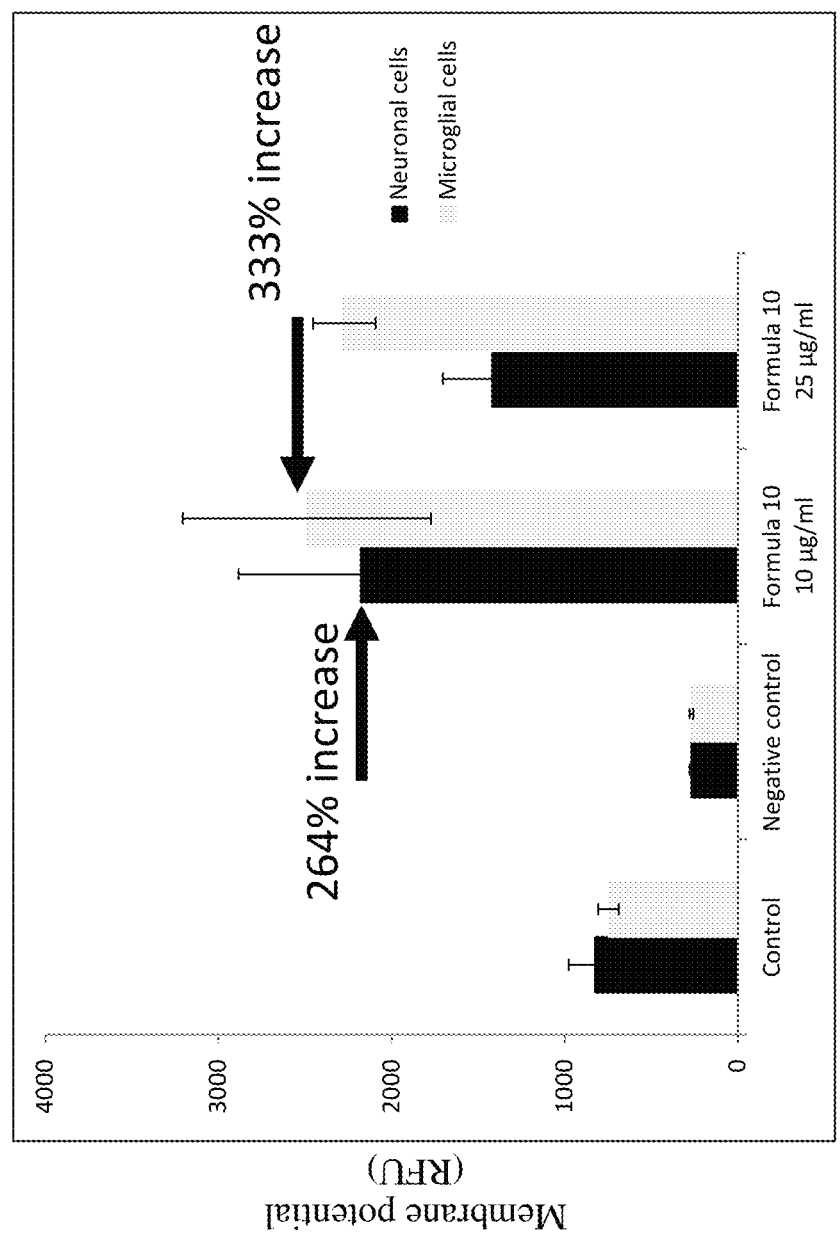
FIG. 10 shows formula 10 improves mitochondrial membrane potential in neuronal and microglial cells.

FIG. 10 shows the effects of Formula 10 on mitochondrial potential. Neuronal and microglial cells were treated with the Formula 10 for 16 hrs, followed by measurement of their mitochondrial membrane potential using TMRE mitochondrial membrane potential assay kit; negative control: 20 µM FCCP (carbonyl cyanide 4-(trifluoromethoxy) phenylhydrazone) which is an ionophore uncoupler of oxidative phosphorylation (OXPHOS). In this experiment Formula 10 improved mitochondrial membrane potential.

Figure 11:
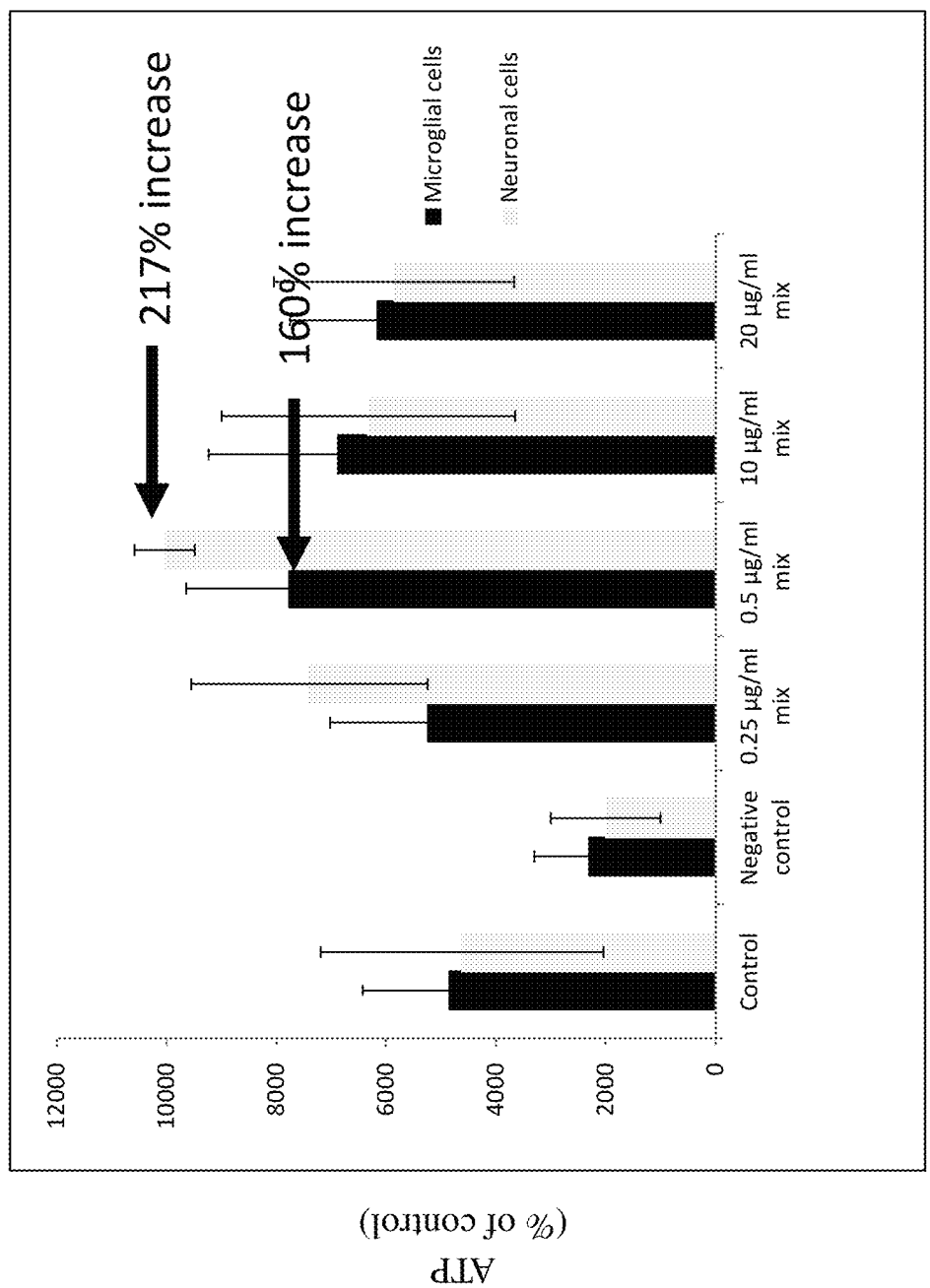
FIG. 11 shows formula 10 supports ATP production.

FIG. 11 shows the effects of Formula 10 on ATP synthesis. Microglial cell line (IMG) and neuronal cell line (SH-SY5Y) were treated with the Formula 10 for 24 hrs and subjected to Luminescent ATP detection Assay kit. Negative control: dead cells exposed to 1 mM $H_2O_2$. The results confirm stimulating effects of Formula 10 in supporting ATP production.

Figure 12:
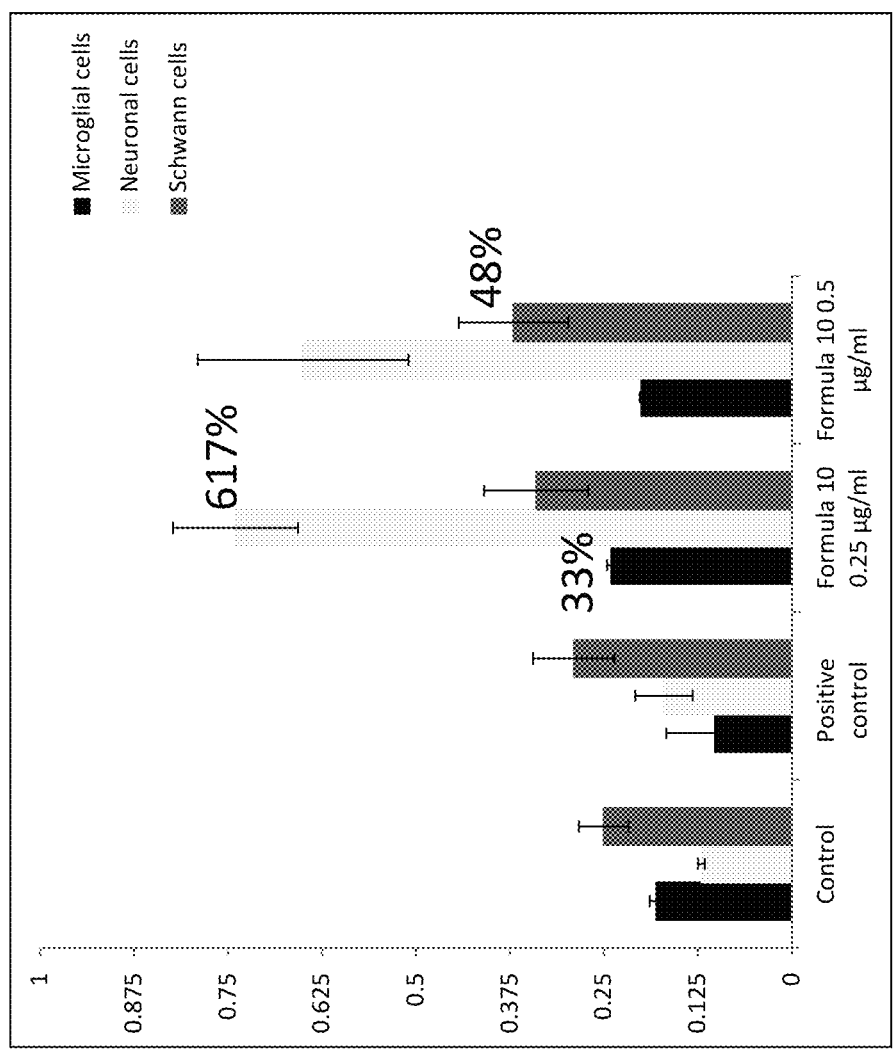
FIG. 12 shows formula 10 increases BDNF in various nervous system cells.

FIG. 12 shows that Formula 10 had the highest stimulatory effect on BDNF secretion in neuronal cells (617%) followed by Schwann cells (48% increase) and microglial cells (33% increase). Neuronal, microglial, and Schwann cells were treated with the Formula 10 for 24 hrs, followed by measurement of BDNF level using colorimetric assay; positive control: curcumin at 25 µg/ml concentration.

Figures 13A, 13B:
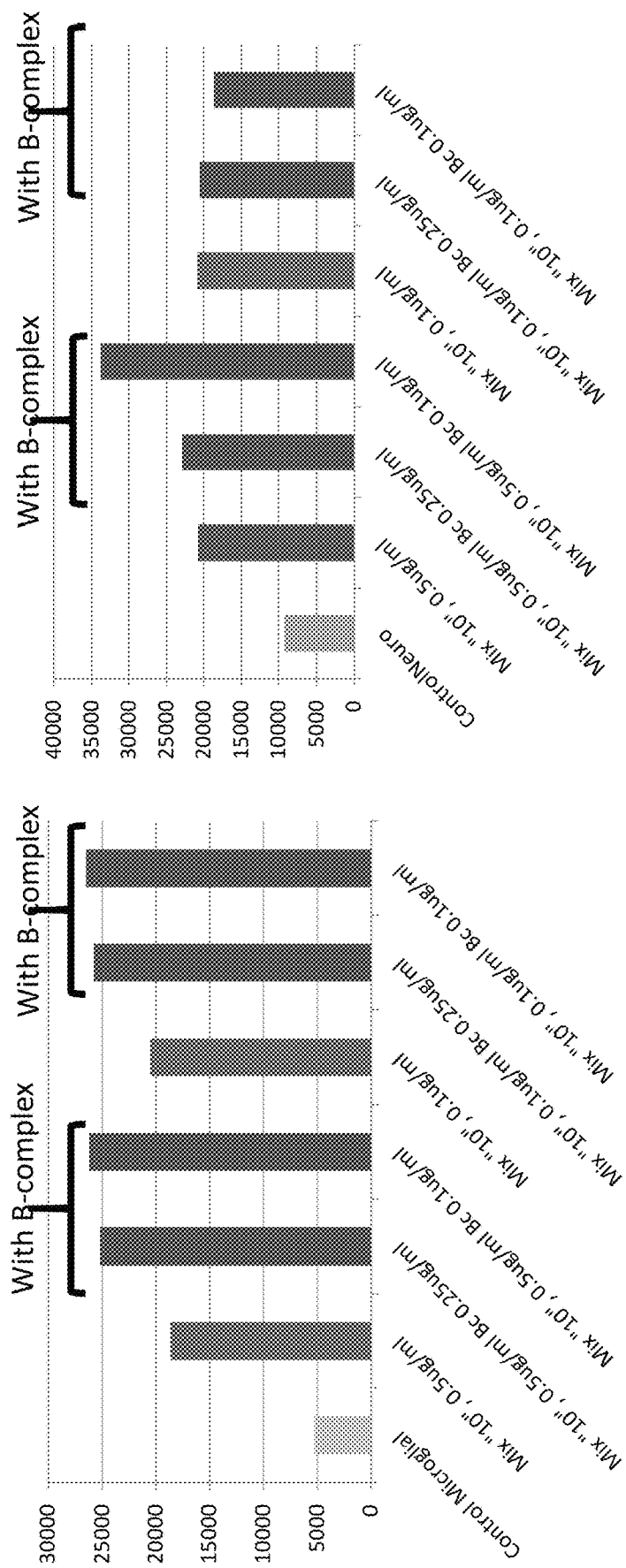
FIGS. 13A and 13B shows formula 10 supports ATP synthesis.

FIGS. 13A and 13B shows combination of formula 10 with vitamin B-complex increases ATP synthesis in microglial and neuronal cells. We did not observe any beneficial effect due to addition of vitamin B-complex.

FIGS. 14A, 14B and 14C shows effects of combination of different concentrations of formula 10 with B complex on mitochondrial biogenesis in microglial cells. FIGS. 15A, 15B and 15C shows effects of combination of different concentrations of formula 10 with B complex on COX-1 in microglial cells. Combination of Formula 10 with B-complex had stimulatory effects on ATP production in microglial and neuronal cells. Slightly enhanced mitochondrial biogenesis (SDH-A and COX-1) was observed in neuronal but not in microglial cells exposed to B-complex with Formula 10, compared to Formula 10 used alone.

FIGS. 16A, 16B and 16C shows effects of combining different concentrations of Formula 10 with B complex on mitochondrial biogenesis in neuronal cells. FIGS. 17A, 17B and 17C shows Effects of combining different concentrations of Formula 10 with B complex on COX-1 in neuronal cells. Combination of Formula 10 with B-complex had stimulatory effects on ATP production in microglial and neuronal cells. Slightly enhanced mitochondrial biogenesis (SDH-A and COX-1) was observed in neuronal but not in microglial cells exposed to B-complex with Formula 10, compared to Formula 10 used alone.

Figure 18:
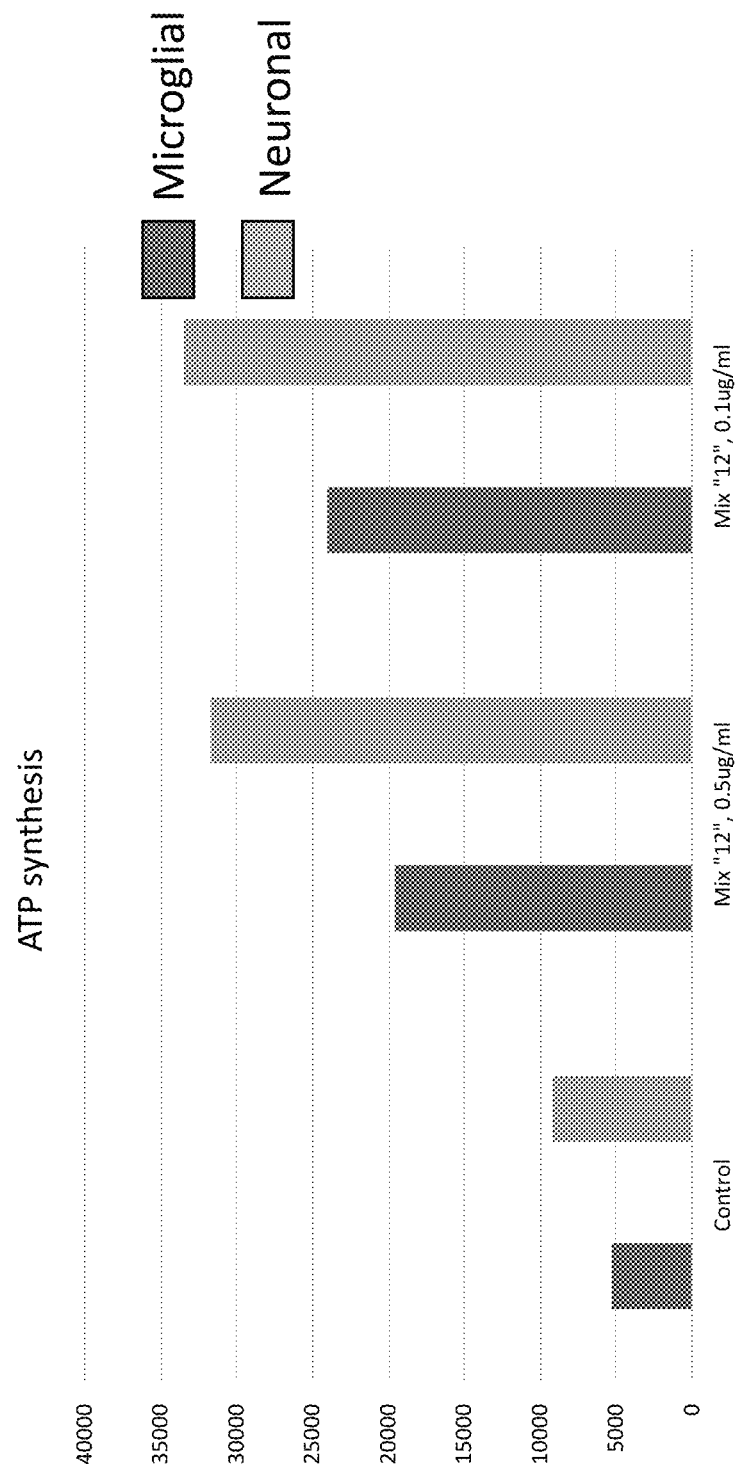
FIG. 18 shows effects of formula 12 on ATP synthesis in microglial and neuronal cells.

FIG. 18 shows effects of formula 12 on ATP synthesis in microglial and neuronal cells. To test the efficacy of formula 12 Following test were conducted to evaluate the effects of Formula 12 on important markers associated with healthy nerve system function: Bioenergy: ATP synthesis, Mitochondrial function: Mitochondrial biogenesis, Neuroplasticity: Brain-derived neurotrophic factor (BDNF) secretion. Formula 12 has shown concentration dependent stimulatory effects on ATP synthesis both in microglial and neuronal cells.

Figure 19:
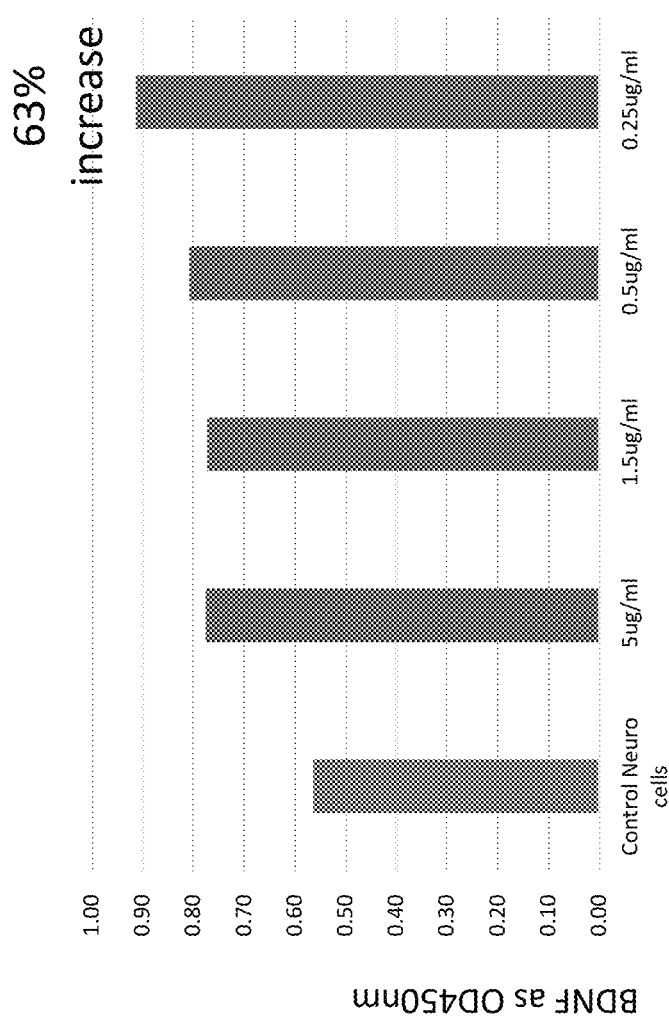
FIG. 19 shows effects of Formula 12 on BDNF secretion by neuronal cells.

Cell lines used in the experiments: Neuronal cells SY-SK5Y, Microglial cells IMG. Additional tests include the effects of a combination of Formula 12 with vitamin B complex on ATP production and mitochondrial biogenesis FIG. 19 shows effects of Formula 12 on BDNF secretion by neuronal cells. Formula 12 had stimulatory effects on BDNF secretion by neuronal cells. In the presence of Formula 12 at 0.25 ug/ml concentration the secretion of BDNF increased by 63%. With increased Formula 12 concentrations the BDNF secretion by neuronal cells gradually decreased. However, at 5 µg/ml the BDNF secretion was still 39% higher compared to control cells.

FIGS. 20A and 20B shows effects of Formula 12 on mitochondrial biogenesis in microglial cells and neuronal cells. FIGS. 21A and 21B shows effects of Formula 12 on COX-1 mitochondrial biogenesis in microglial cells and neuronal cells. In microglial cells, Formula 12 showed concentration dependent stimulatory effects on nuclear encoded SDH-A mitochondrial enzyme, with 58% increase at 25 µg/ml. It had a slight 5% stimulatory effect on COX-1 at 25 µg/ml. In neuronal cells the lowest tested concentration of Formula 12 increased SDH-A by 71%, but at higher concentrations the stimulatory effects decreased. Cox1 in neuronal cells was slightly higher in the presence of 5 ug/ml of Formula 12 compared to control. Its higher concentration was inhibitory.

In order to increase cellular efficacy of Formula 12, we investigated the effects of combining Formula 12 with vitamin B-complex on important nervous system parameters: ATP synthesis and mitochondrial biogenesis in neuronal and microglial cells.

Figure 22:
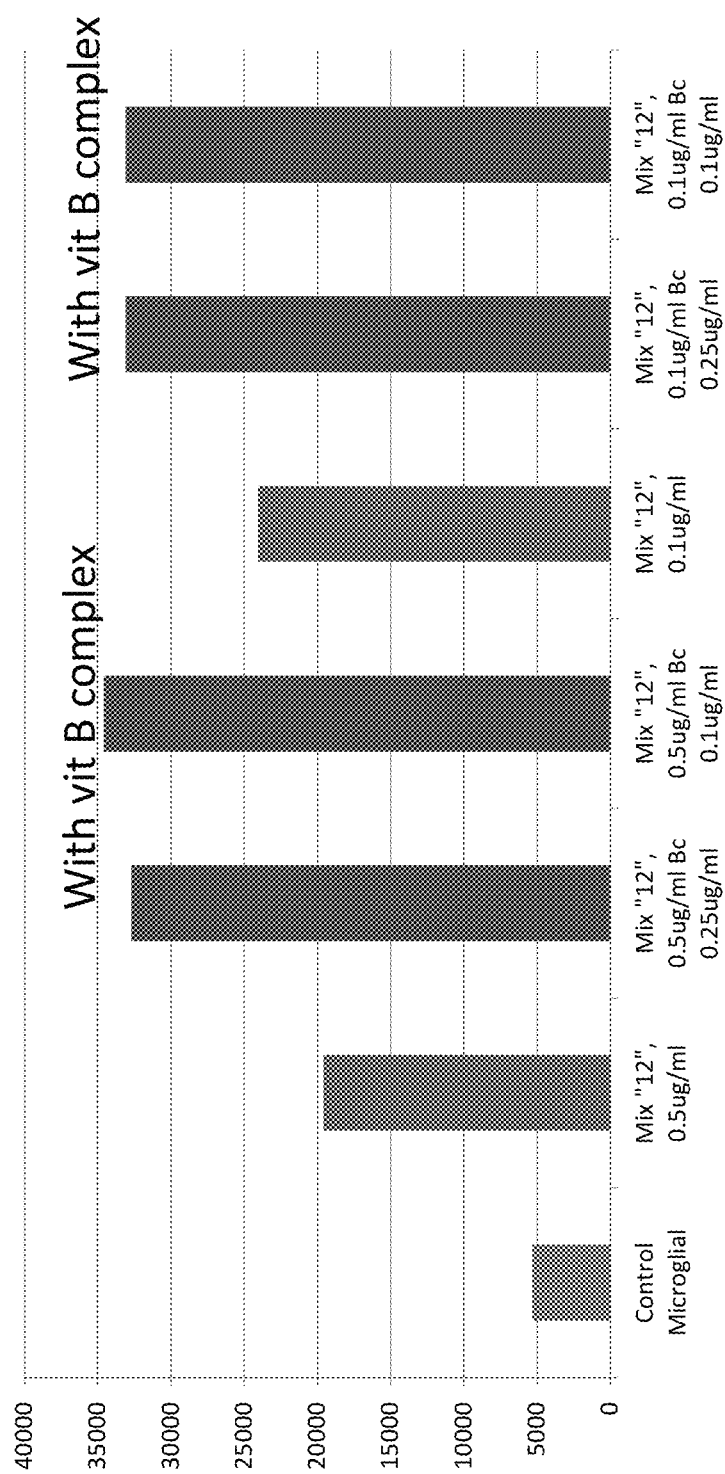
FIG. 22 shows effects of formula 12 with and without vitamin B-complex on ATP synthesis in microglial cells.
Figure 23:
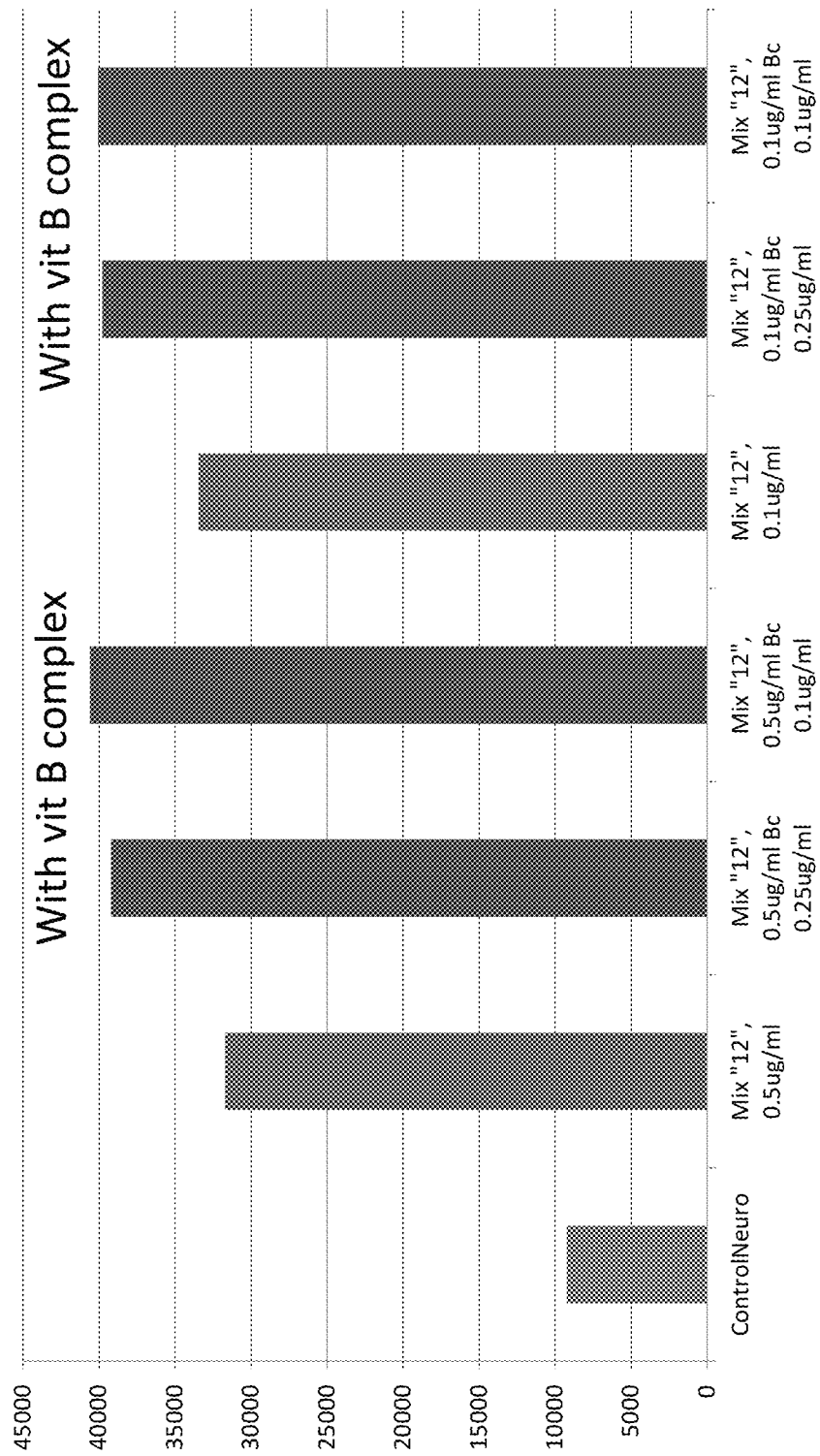
FIG. 23 shows efficacy of formula 12 with and without vitamin B-complex on ATP synthesis in neuronal cells.

FIG. 22 shows effects of formula 12 with and without vitamin B-complex on ATP synthesis in microglial cells. FIG. 23 shows efficacy of formula 12 with and without vitamin B-complex on ATP synthesis in neuronal cells. The combination of Formula 12 with B complex at 0.1 and 0.25 µg/ml concentrations further increased ATP synthesis. The enhancing effects of vitamin B complex applied at 0.1 and 0.25 µg/ml were not concentration dependent suggesting their saturation levels.

FIGS. 24A, 24B and 24C shows effect of adding B complex for improving the efficacy of Formula 12 on mitochondrial biogenesis in microglial cells. In microglial cells: The combination of B-complex with different concentrations of Formula 12 had either no or slightly inhibitory effects on SHD-A compared to Formula 12 applied individually, but still higher than in control cells. Adding B-complex to Formula 12 did not affect COX-1.

FIGS. 25A, 25B and 25C shows effect of adding B complex for improving the efficacy of Formula 12 on COX-1 mitochondrial biogenesis in microglial cells.

FIGS. 26A, 26B and 26C shows effect of adding B complex for improving the efficacy of Formula 12 on mitochondrial biogenesis in neuronal cells. FIGS. 27A, 27B and 27C shows effect of adding B complex for improving the efficacy of Formula 12 on COX-1 mitochondrial biogenesis in neuronal cells. In neuronal cells: Vitamin B-complex combined with Formula 12 demonstrated highly significant stimulatory effects on mitochondrial biogenesis as evaluated by SDH-A and COX-1 at all Formula 12 concentrations. Overall conclusions on the effects of B-complex applied together with formula 12 is that combination of B-complex with Formula 12 was beneficial in increasing ATP synthesis in both microglial and neuronal cells. Its combination was highly effective in stimulating mitochondrial biogenesis in neuronal, but not in microglial cells.

Figure 28:
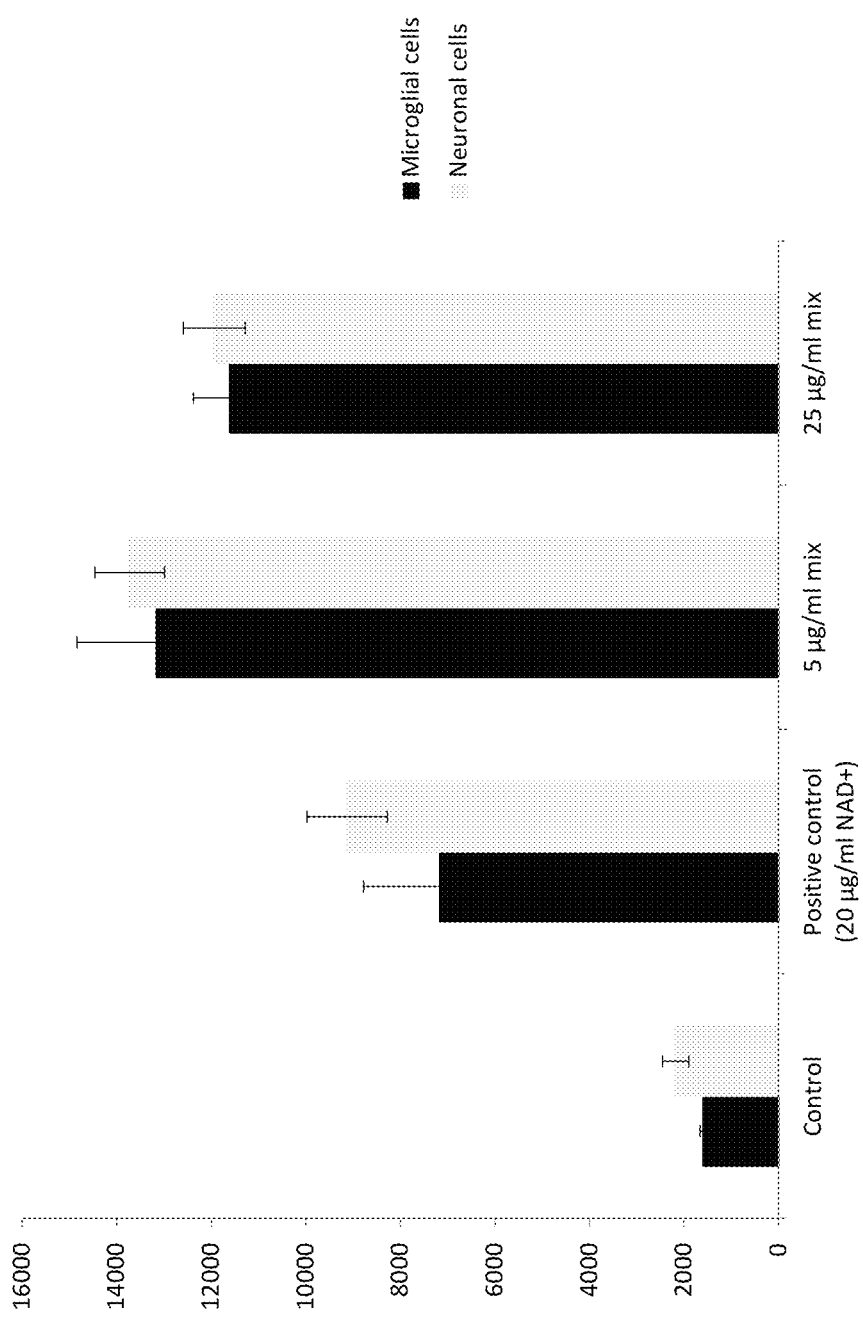
FIG. 28 shows formula 5 supports ATP synthesis.

FIG. 28 shows formula 5 supports ATP synthesis. The figure shows In vitro ATP production assay. Four different cell lines were stimulated with 5 and 25 µg/ml concentrations of Formula 5 for 16 hrs at 37° C. and subjected to CellTiter-Glo Luminescence Cell Viability Assay. Values shown are mean±standard deviation (n=6). Mitochondria are essential organelles for various cellular processes that include ATP production, intracellular $Ca^{2+}$ signaling, and generation of reactive oxygen species. Mitochondrial dysfunction has been linked to many diseases including various neurodegenerative diseases, diabetes, cancer and it has been associated with aging.

Neurons critically depend on mitochondrial function to establish membrane excitability and to execute the complex processes of neurotransmission and plasticity. Because mitochondrial biogenesis involves mtDNA replication, mitochondria cannot be made de novo but must derive from other mitochondria. We evaluated mitochondria biogenesis by measuring levels of two important mitochondrial proteins that are commonly used as mitochondrial biogenesis markers: Nuclear DNA encoded SDHA (Flavoprotein (FP) subunit A of succinate dehydrogenase. Succinate dehydrogenase functions both in Krebs cycle and electron transport chain as Complex II and Mitochondrial DNA (mtDNA) encoded COX-1 (cytochrome C oxidase I).

In vitro biogenesis assay. Four different cell lines stimulated with 5 and 25 µg/ml concentrations of Core Formula 5 for 16 hrs at 37° C. and subjected to MitoBiogenesis In-Cell ELISA assay.

Brain-derived neurotrophic factor (BDNF) is a key factor in the survival of nerve cells (neurons). It plays important role in the growth, maturation (differentiation), and maintenance of these cells. BDNF is needed in the formation of appropriate synaptic connections in the brain, and disruptions in this process contribute to disorders of cognitive function, such as learning and memory. Because of its fundamental role in numerous neurological functions in the central nervous system, BDNF is a recognized biomarker of nervous system function and established target in investigating drugs for neurodegenerative and neuropsychiatric disorders.

Figure 30:
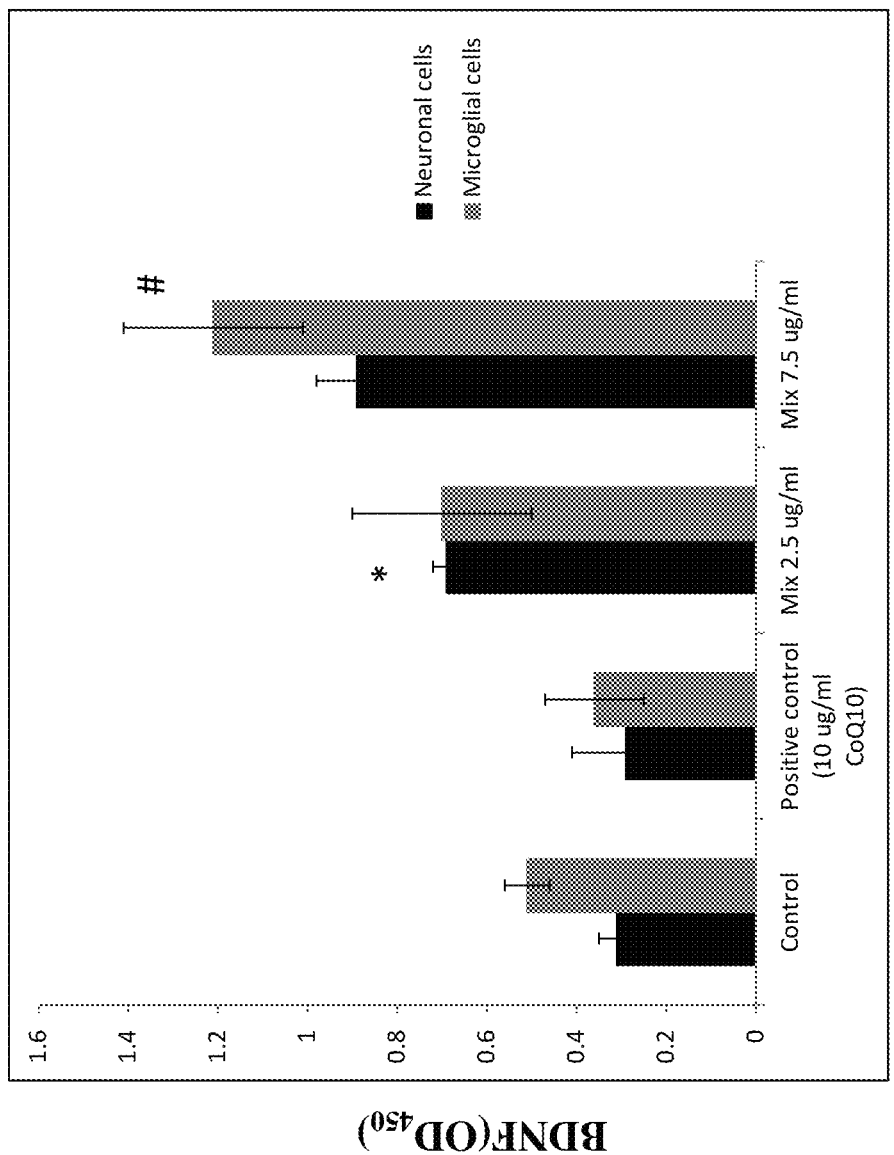
FIG. 30 shows formula 5 significantly increases BDNF secretion in neuronal and microglial cells.

FIGS. 29A, 29B, 29C and 29D shows formula 5 significantly stimulates mitochondrial biogenesis in neuronal and microglial cells. FIG. 30 shows formula 5 significantly increases BDNF secretion in neuronal and microglial cells. Formula 5 was effective in stimulating the BDNF secretion in neuronal cells by 187% and in microglial cells by 137% compared to control. In conclusion, formula 5 showed beneficial effects in supporting key metabolic aspects of neuronal and microglial cell functions by: Increasing ATP production, stimulating mitochondrial biogenesis and increasing secretion of BDNF.

Drug formulations suitable for these administration routes can be produced by adding one or more pharmacologically acceptable carrier to the agent and then treating the micronutrient composition through a routine process known to those skilled in the art. The mode of administration includes, but is not limited to, non-invasive peroral, topical (for example, transdermal), enteral, transmucosal, targeted delivery, sustained-release delivery, delayed release, pulsed release and parenteral methods. Peroral administration may be administered both in liquid and dry state. In one embodiment, pharmaceutical micronutrient composition would be more specifically formula 12, 10 and 5.

Formulations suitable for oral administration may be in the form of capsules, cachets, pills, tablets, lozenges (using a flavored bases, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin or sucrose and acacia), each containing a predetermined amount of a subject composition as an active ingredient. Subject compositions may also be administered as a bolus, electuary or paste.

When an oral solid drug product is prepared, pharmaceutical micronutrient composition is mixed with an excipient (and, if necessary, one or more additives such as a binder, a disintegrant, a lubricant, a coloring agent, a sweetening agent, and a flavoring agent), and the resultant mixture is processed through a routine method, to thereby produce an oral solid drug product such as tablets, coated tablets, granules, powder or capsules. Additives may be those generally employed in the art. Examples of excipients include lactate, sucrose, sodium chloride, glucose, starch, calcium carbonate, kaolin, microcrystalline cellulose and silicic acid. Binders include water, ethanol, propanol, simple syrup, glucose solution, starch solution, liquefied gelatin, carboxymethylcellulose, hydroxypropyl cellulose, hydroxypropyl starch, methyl cellulose, ethyl cellulose, shellac, calcium phosphate and polyvinyl pyrrolidone. Disintegrants include dried starch, sodium arginate, powdered agar, sodium hydroxy carbonate, calcium carbonate, sodium lauryl sulfate, monoglyceryl stearate and lactose. Lubricants include purified talc, stearic acid salts, borax and polyethylene glycol. Sweetening agents include sucrose, orange peel, citric acid and tartaric acid.

When a liquid drug product for oral administration is prepared, pharmaceutical micronutrient composition is mixed with an additive such as a sweetening agent, a buffer, a stabilizer, or a flavoring agent, and the resultant mixture is processed through a routine method, to produce an orally administered liquid drug product such as an internal solution medicine, syrup or elixir. Examples of the sweetening agent include vanillin; examples of the buffer include sodium citrate; and examples of the stabilizer include tragacanth, acacia, and gelatin.

For the purposes of transdermal (e.g., topical) administration, dilute sterile, aqueous or partially aqueous solutions (usually in about 0.1% to 5% concentration), otherwise similar to the above parenteral solutions, may be prepared with pharmaceutical micronutrient composition.

Formulations containing pharmaceutical micronutrient composition for rectal or vaginal administration may be presented as a suppository, which may be prepared by mixing a subject composition with one or more suitable non-irritating carriers, comprising, for example, cocoa butter, polyethylene glycol, a suppository wax or a salicylate, which is solid at room temperature, but liquid at body temperature and, therefore, will melt in the appropriate body cavity and release the encapsulated compound(s) and composition(s). Formulations that are suitable for vaginal administration also include pessaries, tampons, creams, gels, pastes, foams or spray formulations containing such carriers as are known in the art to be appropriate.

A targeted-release portion for capsules containing pharmaceutical micronutrient composition can be added to the extended-release system by means of either applying an immediate-release layer on top of the extended release core; using coating or compression processes, or in a multiple-unit system such as a capsule containing extended- and immediate-release beads.

When used with respect to a pharmaceutical micronutrient composition, the term "sustained release" is art recognized. For example, a therapeutic composition that releases a substance over time may exhibit sustained-release characteristics, in contrast to a bolus type administration in which the entire amount of the substance is made biologically available at one time. In particular embodiments, upon contact with body fluids, including blood, spinal fluid, mucus secretions, lymph or the like, one or more of the pharmaceutically acceptable excipients may undergo gradual or delayed degradation (e.g., through hydrolysis), with concomitant release of any material incorporated therein, e.g., a therapeutic and/or biologically active salt and/or composition, for a sustained or extended period (as compared with the release from a bolus). This release may result in prolonged delivery of therapeutically effective amounts of any of the therapeutic agents disclosed herein.

Current efforts in the area of drug delivery include the development of targeted delivery, in which the drug is only active in the target area of the body (for example, mucous membranes such as in the nasal cavity), and sustained-release formulations, in which the pharmaceutical micronutrient composition is released over a period of time in a controlled manner from a formulation. Types of sustained release formulations include liposomes, drug-loaded biodegradable microspheres and pharmaceutical micronutrient composition polymer conjugates.

Delayed-release dosage formulations are created by coating a solid dosage form with a film of a polymer, which is insoluble in the acid environment of the stomach, but soluble in the neutral environment of the small intestine. The delayed-release dosage units can be prepared, for example, by coating a pharmaceutical micronutrient composition with a selected coating material. The pharmaceutical micronutrient composition may be a tablet for incorporation into a capsule, a tablet for use as an inner core in a "coated core" dosage form, or a plurality of drug-containing beads, particles or granules, for incorporation into either a tablet or a capsule. Preferred coating materials include bioerodible, gradually hydrolysable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract, or slowly erode as the dosage form passes through the gastrointestinal tract, while enzymatically degradable polymers are degraded by bacterial enzymes present in the lower gastrointestinal tract, particularly in the colon. Alternatively, a delayed-release tablet may be formulated by dispersing a drug within a matrix of a suitable material such as a hydrophilic polymer or a fatty compound. Suitable hydrophilic polymers include, but are not limited to, polymers or copolymers of cellulose, cellulose ester, acrylic acid, methacrylic acid, methyl acrylate, ethyl acrylate and vinyl or enzymatically degradable polymers or copolymers as described above. These hydrophilic polymers are particularly useful for providing a delayed-release matrix. Fatty compounds for use as a matrix material include, but are not limited to, waxes (e.g., carnauba wax) and glycerol tristearate. Once the active ingredient is mixed with the matrix material, the mixture can be compressed into tablets.

A pulsed-release dosage is one that mimics a multiple dosing profile without repeated dosing, and typically allows at least a twofold reduction in dosing frequency as compared with the drug presented as a conventional dosage form (e.g., as a solution or prompt drug-releasing, conventional solid dosage form). A pulsed-release profile is characterized by a time period of no release (lag time) or reduced release, followed by rapid drug release. These can be formulated for critically ill patients using the instant pharmaceutical micronutrient composition.

The phrases "parenteral administration" and "administered parenterally" as used herein refer to modes of administration other than enteral and topical, such as injections, and include without limitation intravenous, intramuscular, intrapleural, intravascular, intrapericardial, intra-arterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

Certain pharmaceutical micronutrient composition disclosed herein, suitable for parenteral administration, comprise one or more subject compositions in combination with one or more pharmaceutically acceptable sterile, isotonic, aqueous, or non-aqueous solutions, dispersions, suspensions or emulsions, or sterile powders, which may be reconstituted into sterile injectable solutions or dispersions just prior to use, and which may contain antioxidants, buffers, bacteriostats, solutes that render the formulation isotonic within the blood of the intended recipient, or suspending or thickening agents.

When an injection product is prepared, pharmaceutical micronutrient composition is mixed with an additive such as a pH regulator, a buffer, a stabilizer, an isotonicity agent or a local anesthetic, and the resultant mixture is processed through a routine method, to thereby produce an injection for subcutaneous injection, intramuscular injection, or intravenous injection. Examples of the pH regulator or buffer include sodium citrate, sodium acetate and sodium phosphate; examples of the stabilizer include sodium pyrosulfite, EDTA, thioglycolic acid, and thiolactic acid; examples of the local anesthetic include procaine hydrochloride and lidocaine hydrochloride; and examples of the isotonicity agent include sodium chloride and glucose.

Adjuvants are used to enhance the immune response. Various types of adjuvants are available. Haptens and Freund's adjuvant may also be used to produce water-in-oil emulsions of immunogens.

The phrase "pharmaceutically acceptable" is art recognized. In certain embodiments, the term includes compositions, polymers and other materials and/or dosage forms that are within the scope of sound medical judgment, suitable for use in contact with the tissues of mammals, both human beings and animals, without excessive toxicity, irritation, allergic response or other problem or complication, commensurate with a reasonable benefit-risk ratio.

The phrase "pharmaceutically acceptable carrier" is art recognized, and includes, for example, pharmaceutically acceptable materials, compositions or vehicles, such as a liquid or solid filler, diluent, solvent or encapsulating material involved in carrying or transporting any subject composition from one organ or portion of the body, to another organ or portion of the body. Each carrier must be "acceptable" in the sense of being compatible with the other ingredients of a subject composition, and not injurious to the patient. In certain embodiments, a pharmaceutically acceptable carrier is non-pyrogenic. Some examples of materials that may serve as pharmaceutically acceptable carriers include: (1) sugars, such as lactose, glucose and sucrose; (2) starches, such as corn starch and potato starch; (3) cellulose and its derivatives, such as sodium carboxymethyl cellulose, ethyl cellulose and cellulose acetate; (4) powdered tragacanth; (5) malt; (6) gelatin; (7) talc; (8) cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In certain embodiments, the pharmaceutical micronutrient compositions described herein are formulated in a manner such that said compositions will be delivered to a mammal in a therapeutically effective amount, as part of a prophylactic, preventive or therapeutic treatment to overcome the infection caused by corona viruses (irrespective of the type).

In certain embodiments, the dosage of the pharmaceutical micronutrient compositions, which may be referred to as therapeutic composition provided herein, may be determined by reference to the plasma concentrations of the therapeutic composition or other encapsulated materials. For example, the blood samples may be tested for their immune response to their corresponding viral load or lack thereof.

The therapeutic pharmaceutical micronutrient composition provided by this application may be administered to a subject in need of treatment by a variety of conventional routes of administration, including orally, topically, parenterally, e.g., intravenously, subcutaneously or intramedullary. Further, the therapeutic compositions may be administered intranasally, as a rectal suppository, or using a "flash" formulation, i.e., allowing the medication to dissolve in the mouth without the need to use water. Furthermore, the compositions may be administered to a subject in need of treatment by controlled-release dosage forms, site-specific drug delivery, transdermal drug delivery, patch-mediated drug delivery (active/passive), by stereotactic injection, or in nanoparticles.

Expressed in terms of concentration, an active ingredient can be present in the therapeutic compositions of the present invention for localized use via the cutis, intranasally, pharyngolaryngeally, bronchially, intravaginally, rectally or ocularly.

For use as aerosols, the active ingredients can be packaged in a pressurized aerosol container together with a gaseous or liquefied propellant, for example dichlorodifluoromethane, carbon dioxide, nitrogen, propane and the like, with the usual adjuvants such as cosolvents and wetting agents, as may be necessary or desirable. The most common routes of administration also include the preferred transmucosal (nasal, buccal/sublingual, vaginal, ocular and rectal) and inhalation routes.

In addition, in certain embodiments, the subject pharmaceutical micronutrient composition of the present application may be lyophilized or subjected to another appropriate drying technique such as spray drying. The subject compositions may be administered once, or may be divided into a number of smaller doses to be administered at varying intervals of time, depending in part on the release rate of the compositions and the desired dosage.

Formulations useful in the methods provided herein include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of a subject pharmaceutical micronutrient composition that may be combined with a carrier material to produce a single dose may vary depending upon the subject being treated and the particular mode of administration.

The therapeutically acceptable amount described herein may be administered in inhalant or aerosol formulations. The inhalant or aerosol formulations may comprise one or more agents, such as adjuvants, diagnostic agents, imaging agents, or therapeutic agents useful in inhalation therapy. The final aerosol formulation may, for example, contain 0.005-90% w/w, for instance 0.005-50%, 0.005-5% w/w, or 0.01-1.0% w/w, of medicament relative to the total weight of the formulation.

Examples of suitable aqueous and non-aqueous carriers that may be employed in the pharmaceutical micronutrient composition include water, ethanol, polyols (such as glycerol, propylene glycol, polyethylene glycol and the like), and suitable mixtures thereof, vegetable oils such as olive oil, and injectable organic esters such as ethyl oleate. Proper fluidity may be maintained, for example by the use of coating materials such as lecithin, by the maintenance of the required particle size in the case of dispersions, and by the use of surfactants.

What is claimed is:

1. A pharmaceutical micronutrient composition, consisting of:

*Avena sativa* in the range of 1 mg to 50,000 mg, Coenzyme Q10 in the range of 10 mcg to 20,000 mg, NAD+ in the range of 0.1 mg to 20,000 mg, American Ginseng in the range of 1 mg to 50,000 mg, and Pyrroloquinoline quinone in the range of 0.1 mg to 50,000 mg formulated as a tablet, coated tablet, capsule, pill, lozenges, emulsion, pastilles, suppository, or paste.

2. The pharmaceutical micronutrient composition according to claim 1, wherein the pharmaceutical micronutrient composition is used for a treatment of cognitive impairment, depression and other nervous system problems in the human and other species.

3. The pharmaceutical micronutrient composition according to claim 2, wherein a cognitive impairment is linked to mitochondrial dysfunction.

4. The pharmaceutical micronutrient composition according to claim 2, wherein a cognitive impairment is linked to dysfunction in BDNF secretion.

5. The pharmaceutical micronutrient composition according to claim 2, wherein a cognitive impairment is linked to exposure to excessive stress due to mental and chemical conditions.

6. The pharmaceutical micronutrient composition according to claim 1, wherein the pharmaceutical micronutrient composition is used for maintaining healthy function of the nervous system in the human and other species.

7. The pharmaceutical micronutrient composition according to claim 1, wherein the pharmaceutical micronutrient composition is used for preventing and mitigating the decline in cognitive and behavioral abilities due to age and other external and internal factors, wherein the pharmaceutical micronutrient composition is used for maintaining healthy function of the nervous system in the human and other species.

8. The pharmaceutical micronutrient composition of claim 1, wherein the American Ginseng is from natural source as a whole plant, an extract or a combination thereof and Coenzyme Q10 is from a natural source and synthetic source.

9. The pharmaceutical micronutrient composition of claim 1, wherein the NAD+ is from a natural source, synthetic source or a combination thereof, Pyrroloquinoline quinone is from a natural source, synthetic source or a combination thereof.

* * * * *